United States Patent
Dhere et al.

(10) Patent No.: US 11,235,054 B2
(45) Date of Patent: Feb. 1, 2022

(54) MULTIVALENT VACCINE COMPOSITION

(71) Applicants: Serum Institute of India Private Limited, Pune Maharashtra (IN); The United States of America, as Represented by the Secretary, Department of Health and Human Services, Bethesda, MD (US)

(72) Inventors: Rajeev Mhalasakant Dhere, Pune Maharashtra (IN); Sambhaji Shankar Pisal, Pune Maharashtra (IN); Jagdish Kamalaji Zade, Pune Maharashtra (IN); Rajendra Narayan Sabale, Pune Maharashtra (IN); Ravindra Bapurao Kadam, Pune Maharashtra (IN); Abhijeet Sanjeev Kamble, Pune Maharashtra (IN); Baoming Jiang, Bethesda, MD (US); Roger Glass, Bethesda, MD (US)

(73) Assignees: Serum Institute of India Private Limited, Pune Maharashtra (IN); The United States of America, as Represented by the Secretary, Department of Health and Human Services, Bethesda, MD (US)

( * ) Notice: Subject to any disclaimer, the term of this patent is extended or adjusted under 35 U.S.C. 154(b) by 181 days.

(21) Appl. No.: 16/327,513

(22) PCT Filed: Aug. 24, 2017

(86) PCT No.: PCT/IB2017/055100
§ 371 (c)(1),
(2) Date: Feb. 22, 2019

(87) PCT Pub. No.: WO2018/037365
PCT Pub. Date: Mar. 1, 2018

(65) Prior Publication Data
US 2019/0175722 A1    Jun. 13, 2019

(30) Foreign Application Priority Data
Aug. 26, 2016 (IN) .............................. 201621029037

(51) Int. Cl.
A61K 39/00 (2006.01)
C12N 7/00 (2006.01)
*A61K 39/13* (2006.01)
A01N 1/02 (2006.01)
*A61K 39/085* (2006.01)
*A61K 39/15* (2006.01)
*A61K 39/12* (2006.01)
*A61K 39/02* (2006.01)

(52) U.S. Cl.
CPC ............ *A61K 39/15* (2013.01); *A61K 39/099* (2013.01); *A61K 39/12* (2013.01); *A61K 39/13* (2013.01); *A61K 2039/5252* (2013.01); *A61K 2039/545* (2013.01); *A61K 2039/55505* (2013.01); *A61K 2039/55544* (2013.01); *C12N 2720/12334* (2013.01); *C12N 2770/32634* (2013.01); *Y02A 50/466* (2018.01)

(58) Field of Classification Search
CPC ............ C12Q 1/6806; C12Q 2521/537; C12Q 2527/125; A61P 37/04; A61K 39/12
See application file for complete search history.

(56) References Cited

FOREIGN PATENT DOCUMENTS

WO    WO2012093406    * 7/2012

* cited by examiner

*Primary Examiner* — Barry A Chestnut
(74) *Attorney, Agent, or Firm* — Nath, Goldberg & Meyer; Joshua B. Goldberg; Stephanie F. Majkut

(57) ABSTRACT

Stable, immunogenic combination vaccine(s) comprising a mixture of antigens for prevention and prophylaxis of infections caused by Rotavirus, Poliomyelitis virus, Haemophilus influenzae, Corynebacterium diphtheriae, Clostridium tetani, Bordetella pertussis and Hepatitis B virus. A multivalent combination vaccine comprises i) significantly dose-reduced Salk-IPV or Sabin-IPV (IPV) antigens prepared by methods of formaldehyde inactivation and alum hydroxide adsorption resulting in maximum D-antigen recovery; ii) Injectable heat inactivated Rotavirus antigen(s) providing broad cross-protective immunity among human rotavirus strains; iii) Hib PRP-carrier protein conjugate having improved stability and immunogenicity; iv) whole cell pertussis antigen with improved immunogenicity and stability; and v) Homogenous fractions of Diphtheria and Tetanus toxoids. Such stable and immunogenic vaccine compositions are made by i) individually adsorbing dose reduced IPV, IRV antigens on alum hydroxide and keeping other antigen(s) unadsorbed or adsorbed on alum phosphate, alum hydroxide, or a combination thereof; and ii) using an order of addition of antigens during blending.

38 Claims, 1 Drawing Sheet

X Axis: Volume (ml)
Y Axis: UV@280nm (mAU)
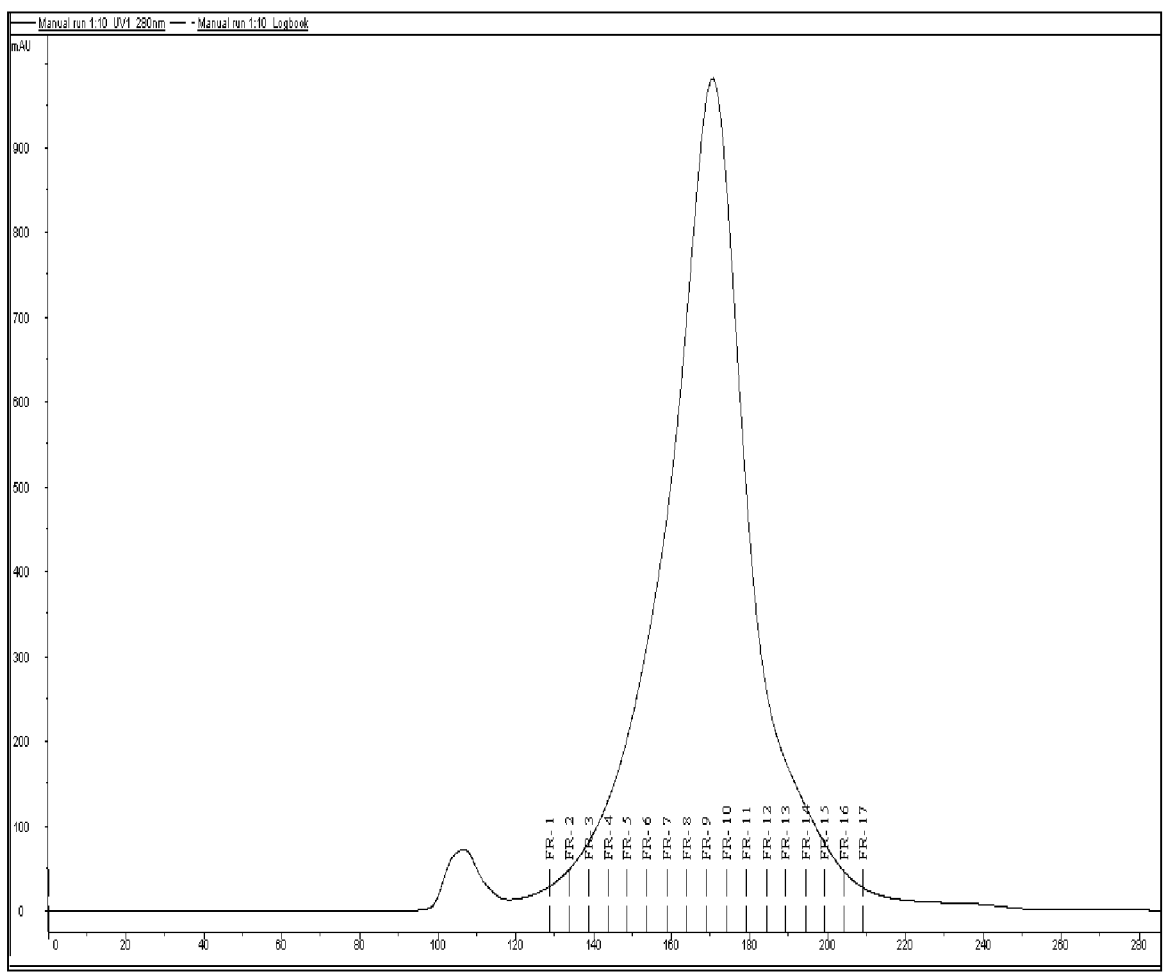

MULTIVALENT VACCINE COMPOSITION

This is a National Phase Application filed under 35 U.S.C. 371 as a national stage of PCT/IB2017/055100, filed Aug. 24, 2017, and claims priority benefit from Indian Application No. 201621029037, filed Aug. 26, 2016, the content of each is hereby incorporated by reference in its entirety.

FIELD OF THE INVENTION

The present invention relates to stable combination vaccine(s) comprising a mixture of antigens for prevention and prophylaxis of infections caused by Rotavirus, poliomyelitis virus, Haemophilus influenzae, Corynebacterium diphtheriae, Clostridium tetani, Bordetella pertussis (whole cell) and Hepatitis B virus. The invention in particular relates to a stable multivalent combination vaccine comprising of significantly dose reduced Salk IPV or Sabin IPV (IPV) antigens and injectable heat inactivated Rotavirus antigen(s) obtained from Rotavirus (CDC-9) strains.

BACKGROUND OF THE INVENTION

The poliovirus invades the nervous system and can cause irreversible paralysis in a matter of hours. Three types of poliovirus exist globally i.e. Type 1, Type 2, & Type 3.

The prevalence of polio virus has largely been decreased by the use of Oral Polio Vaccine (OPV), based on live-attenuated Sabin polio strains. However, OPV has limitations for the post-eradication era. OPV contains circulating vaccine-derived polioviruses (cVDPVs) which are transmissible and can become neurovirulent (similar to wild polioviruses) resulting in vaccine associated paralytic poliomyelitis. Such strains can potentially re-seed the world with polioviruses and negate the eradication accomplishments. To prevent the emergence of circulating vaccine-derived polioviruses (cVDPVs), WHO's Strategic Advisory Group of Experts (SAGE) has recommended at least one dose of IPV along with Oral Polio Vaccine (OPV) in countries currently using OPV. (Ref: World Health Organization. Meeting of the Strategic Advisory Group of Experts on Immunization, November 2012—conclusions and recommendations. Wkly Epidemiol Rec 2013; 88:1-16; PMID: 23311010).

Presently, IPV is made using wild polio strain i.e. Salk strain and the newer sabin strains which is made from the same attenuated Sabin strains as those used in the live attenuated OPV. The approved standard dose of polio vaccines delivered by intramuscular (IM) or deep subcutaneous (SC) injection contains D antigens as 40 Units of inactivated poliovirus type 1 (Mahoney), 8 units of inactivated poliovirus type 2 (MEF-I) and 32 units of inactivated poliovirus type 3 (Saukett) (e.g. Infanrix-IPV™). But IPV has high production costs as compared to OPV, mainly due to requirements for more virus per dose; additional downstream processing (i.e. concentration, purification and inactivation), and the related QC-testing; loss of antigen or poor recovery in downstream; and containment.

The production costs of IPV is currently estimated to be about 20-fold more expensive than OPV. The future global demand for IPV following eradication of polioviruses could increase from the current level of 80 million doses to 450 million doses per year. Therefore to reduce the final cost of IPV, efforts are undergoing to reduce the quantity of antigenic components i.e. to produce dose reduced IPV formulations.

Globally, Rotavirus is the leading cause of severe acute diarrhea and vaccine is found a promising solution to reduce the disease burden. It has been estimated that the number of rotavirus deaths in the world declined from 528 000 to 215 000 during thirteen years from 2000 to 2013, since rotavirus vaccine had been introduced in >60 countries . Out of that, an estimated 47 100 (22%) rotavirus deaths occurred in India in 2013. India, Nigeria, Pakistan, and Democratic Republic of Congo, these four countries accounted for approximately half (49%) of all estimated rotavirus deaths in 2013 .

In recent studies carried worldwide, it is observed that 4 serotypes of rotavirus i.e. G1, G2, G3 and G4 represents over 88% of the strains analyzed globally. The G1 serotype of rotavirus A is one of the most common forms of the virus which cause the disease worldwide, whereas serotype G9 viruses associated have been emerging since the late 1990s and now represent approximately 4% of global isolates. Vaccination against rotavirus-mediated disease is one strategy for addressing this significant health problem. The two currently licensed oral rotavirus vaccines, RotaTeq and Rotarix, which are very effective in reducing cases of severe diarrhea among children in developed and middle income countries, are much less efficacious (~50%) in low income countries of Africa and Asia. [Refer Tate JE et al. "Sustained decline in rotavirus detections in the United States following the introduction of rotavirus vaccine in 2006. Pediatr Infect Dis J 2011; 30:S30-4; and Yen C et al. "Decline in rotavirus hospitalizations and health care visits for childhood diarrhea following rotavirus vaccination in El Salvador". Pediatr Infect Dis J 2011; 30:S6-10]. In addition, the two current rotavirus vaccines have been associated with a risk of intussusception among vaccinated infants. [Refer Patel MM et al. "Intussusception risk and health benefits of rotavirus vaccination in Mexico and Brazil. N Engl J Med 2011; 364:2283-92 and Buttery JP et al. "PAEDS/APSU Study Group. Intussusception following rotavirus vaccine administration: post-marketing surveillance in the National Immunization Program in Australia". Vaccine 2011; 29:3061-6].

One of the candidate Rotavirus vaccine of Bharat Biotech International is based on a 116E rotavirus strain, G9P[11] which is a naturally occurring reassortant containing one bovine rotavirus gene P[11] and ten human rotavirus genes. The protection offered by this vaccine during the first 2 years of life is against the array of circulating genotypes including G1P[8], G2P[4], G12P[6], G12P[8] and G9P[4].Thus it fails to provide cross protection for other strains like G3,G4,G5, G6,G8, G10, G11,G13 and G14. Also the efficacy of 116E based vaccine in the first 2 years of life has been modest (48 to 55%) as it is for other licensed vaccines. [Refer Nita Bhandari et al. "Efficacy of a monovalent human-bovine (116E) rotavirus vaccine in Indian children in the second year of life"; Vaccine. 2014 Aug 11;32 Suppl 1:A110-6]. Also, preclinical testing of several other intramuscularly administered IRV candidates that were based on G1, G3 or G6 have only shown partial protection.

Also inactivation of Rotavirus with β-propiolactone (BPL), an agent commonly used for the inactivation of many viruses, has been shown to cause severe damage to the integrity and biochemical composition of rotavirus particles. In addition, BPL-treated rotavirus showed reduced viral hemagglutinating activity and intramuscular injection with this material in mice evoked less neutralizing antibody than immunization with live virus. [Refer Offit PA et al "Noninfectious rotavirus (strain RRV) induces an immune response in mice which protects against rotavirus challenge". J Clin Microbiol 1989; 27:885-8].

In many parts of the world, immunization with IPV has already replaced OPV so that in a few years, rotavirus vaccine will be the only vaccine administered orally adding to delivery costs. Several operational and logistic considerations thus favor an IRV for use in both developing and industrialized countries.

The appearance of dimers in D/T, seems to be a consequence of the detoxification process by formalin. The existence of dimers can affect the efficiency of the conjugation process—presumably through steric hindrance at the protein surface—leading to a loss of activity, and it is considered desirable that the level of monomers should not drop below 80%. Previously, it has been reported that T with at least 60% monomer can be obtained by using HIC followed by Ion exchange; T with 73% monomer content can be obtained by using only HIC Phenyl sepharose, T with 55% monomer content can be obtained by using only Ammonium sulphate. Therefore an alternative single step method is needed to obtain D/T having at least 80% monomer.

Combination vaccines comprises of two or more vaccines that could be given individually and put them into a single composition. Vaccinee gets the same protection as they do from individual vaccines given separately, but with fewer shots. A combination vaccine thus provides immunogenicity against large number of diseases and is always advantageous over the monovalent vaccines as the compliance is increased by reducing the number of separate vaccinations.

A heptavalent combination vaccine is being developed by Bharat Biotech International that consists of D, T, Acellular pertussis, Sabin IPV (type 1: 40 DU, type 2: 8 DU, type 3: 32DU), Single strain inactivated Rotavirus (G9 strain i.e. 116E strain), a conjugate Haemophilus influenza type b PRP conjugate to TT and a Recombinant Hepatitis B vaccine. As discussed earlier, such Heptavalent combination vaccine comprising of 116E based vaccine would fail to provide cross protection for other strains like G3, G4, G5, G6, G8, G10, G11, G13 and G14. Further the efficacy of said IRV component of combination vaccine in the first 2 years of life will be modest (48 to 55%) as it is for other licensed vaccines.

Another combination vaccine, Hexyon® (also called Hexacima® and Hexaxim®) from Sanofi Pasteur, contains aP. This vaccine is likely to be targeted for private markets in Europe and worldwide. Another hexavalent combination vaccine with aP antigen is currently in Phase III clinical studies, developed jointly by Merck and Sanofi Pasteur.

Currently, GSK's Infanrix Hexa® is the only globally marketed hexavalent pediatric combination vaccine containing IPV. This vaccine contains an acellular pertussis (aP) component and is presented in a syringe-plus-lyophilized vial format because of instability of the Hib component. The major barriers for use of Infanrix Hexa® (GSK), in a developing-country setting are the price of the vaccine product, the requirement for reconstitution of a lyophilized form, and concerns regarding effectiveness of an aP vaccine in the developing world. From a cost perspective, aP antigens have historically exceeded the cost of wP antigens by a factor of ten to more than 30 due to manufacturing differences and royalty costs. Thus, use of whole cell pertussis (wP) in multivalent combination vaccines intended for developing countries has become important both because of cost and emerging concerns about the long-term effectiveness of aP vaccines, especially in developing-country settings.

Several multivalent combination vaccines with wP and IPV are under development. However IPV antigens are not compatible with the common vaccine preservative thimerosal, a mercury-containing compound with antibacterial activity, which causes the polio capsid to lose its antigenicity. Thimerosal is used by many vaccine manufacturers in the inactivation of live B. pertussis organisms to make wP vaccine bulks, which is carried through into the final product, but also causes loss of antigenicity of IPV, and therefore IPV may need to be presented in a separate vial from thiomersal-containing wP to retain its potency over time.

GSK's whole-cell combination vaccine (DTwP-IPV-HBV//Hib) is reported to be in several early clinical trials. However the polio immunogenicity of this product was not as good as a comparator vaccine and it was found that the IPV dose would minimally need to be the same as the current standard IPV dose vaccine or may need to be increased.

Reduced-dose efficacious vaccine formulations which provide protection against infection using a lower dose of IPV antigen are desirable in situations where the supply of conventional vaccine is insufficient to meet global needs or where the cost of manufacture of the conventional vaccine prevents the vaccine being sold at a price which is affordable for developing countries. Also the exposure to lower dose of IPV; compared to the existing marketed formulations could be safer. A multivalent combination vaccine could simplify complex pediatric routine immunization schedules, improve compliance, and reduce delivery costs. However, IPV-containing multivalent vaccines have been a technical challenge for vaccine manufacturers since work began in the early 1990s to combine pediatric vaccines.

Instability of Hib antigen in the presence of aluminum adjuvant, more specifically aluminum hydroxide is a major technical issue. Thus the technical challenge that a manufacturer would need to resolve would be the avoidance of different aluminum adjuvants, if the vaccine bulks going into the combination already had been based on different aluminum chemistries. Thus the sequence of addition of antigen becomes an important factor, as mixing of incompatible antigens or adjuvants may lead to undesired physical appearances for the final product (such as extra precipitates and difficulty in re-suspension) further resulting in unacceptance of the final combination vaccine product [Refer Malecker et al 1996, "Factors affecting the ability of experimental vaccines to protect guinea pigs against lethal challenge with Diphtheria Toxin"; presented at WHO/IABS/NIBSC International meeting on the control and standardization of Acellular pertussis Vaccines, UK, Sep. 26-27 1996].

The currently known and available combination vaccines may not contain appropriate formulations of appropriate antigens in appropriate immunogenic forms for achieving desired levels of efficacy and immunogenicity in the susceptible human population, for a number of diseases in one shot. Most importantly, no multivalent combinations with dose reduced IPV (IPV), broadly cross-protective IRV and whole cell pertussis (wP) are commercially available. Given the above discussed scenario with respect to combination vaccines, there remains a distinct need for affordable all liquid multivalent combination vaccine(s) suitable for developing world providing equivalent or improved seroprotection for individual antigens devoid of antigenic interference.

SUMMARY OF INVENTION

The present invention relates to stable, immunogenic combination vaccine(s) comprising a mixture of antigens for prevention and prophylaxis of infections caused by Rotavirus, Poliomyelitis virus, Haemophilus influenzae, Corynebacterium diphtheriae, Clostridium tetani, Bordetella pertussis and Hepatitis B virus. The invention particularly provides a multivalent combination vaccine comprising of i) significantly dose reduced Salk IPV or Sabin IPV (IPV) antigens prepared by utilizing improved methods of formaldehyde inactivation and alum hydroxide adsorption resulting in maximum recovery of D-antigen and ii) Injectable heat inactivated Rotavirus antigen(s) obtained from Rotavirus (CDC-9) strains that provides a broad cross-protective immunity among human rotavirus strains, iii) Hib PRP-carrier protein conjugate having improved stability and immunogenicity wherein said Hib PRP-carrier protein conjugate is initially prepared by using novel conjugation process and subsequently blended at low temperature in presence of a stabilizer for minimizing free PRP release iv) whole cell pertussis antigen with improved immunogenicity and stability obtained by addition of whole cell pertussis antigen at a later stage in a blend thereby minimizing hydrolysis based degradation v) Homogenous fractions of Diphtheria toxoid and Tetanus toxoid obtained by removal of undesirable aggregates by using Gel Permeation chromatography. The process of making such stable and immunogenic vaccine compositions by i) individually adsorbing dose reduced IPV, IRV antigens on alum hydroxide and keeping other antigen(s) either unadsorbed or adsorbed on Alum Phosphate or Alum hydroxide , or a combination of both and ii) using a particular order of addition of antigens during blending is also disclosed. Further, present invention provides affordable combination vaccine(s) suitable for developing world providing equivalent or improved seroprotection for individual antigens devoid of antigenic interference.

FIGURES

FIG. 1: Diphtheria Toxoid Purification - Chromatogram of Gel Filtration Chromatography Sephacryl S-300 HR, Column XK 26/70.

DETAILED DESCRIPTION:

The present invention relates to multivalent combination vaccine(s) comprising of (i) dose reduced inactivated polio virus vaccine selected from sabin or salk strains; (ii) injectable heat inactivated rotavirus CDC-9 strains; and (iii) optionally, one or more antigens selected from D, T, wP HBsAg, Hib PRP-Carrier protein conjugate, Neisseria meningitidis A antigen(s), Neisseria meningitidis C antigen(s), Neisseria meningitidis W-135 antigen(s), Neisseria meningitidis Y antigen(s), Neisseria meningitidis X antigen(s), Streptococcus Pneumoniae antigen(s), Neisseria meningitidis B bleb or purified antigen(s),Staphylococcus aureus antigen(s), Anthrax, BCG, Hepatitis A antigen(s), Hepatitis B antigen, Human papilloma virus, Salmonella Typhi antigen(s) , acellular pertussis , modified adenylate cyclase , Malaria Antigen (RTS,S), Measles, Mumps, Rubella, Dengue, Zika, Ebola, Chikungunya, Japanese encephalitis, Diarrheal antigens, etc.

Components of the Combination Vaccine composition
Inactivated Polio Virus
Polio (Poliomyelitis) is a highly infectious virus. The poliovirus invades the nervous system and can cause irreversible paralysis in a matter of hours. Three types of poliovirus exist globally i.e. Type 1, Type 2, & Type 3.

First embodiment of the present invention comprises of improved methods of Polio virus (salk or sabin strains) inactivation by formaldehyde in presence of TRIS buffer resulting in maximum recovery of D-antigen. Subsequent adsorption of said IPV on aluminum hydroxide provides significantly dose reduced IPV compositions. The instant invention provides an improved process of formalin inactivation and aluminum hydroxide adsorption, wherein the D-Antigen recovery post-inactivation is in the range of 50-80% and percent adsorption of aluminum hydroxide is in the range of 70-99%.

In one of the aspects of the first embodiment, CCL81-VERO (Monkey kidney) cell were used as host cells for the growing of polio virus i.e. sabin and salk strains. After infection of host cells with desired strain of polio virus and incubation of 72 hours, the medium containing the virus and cell debris was pooled and collected in a single container.

In second aspect of the first embodiment, the harvest was subjected to series of filtration (6 μ and 0.45 μ assembly); and filtrate was collected in a glass container. The filtrate was subjected to tangential flow filtration with 100 kDa cassette; diafiltered using phosphate buffer and purified using anion exchange chromatography.

In third aspect of the first embodiment, the purified virus pool was further subjected to buffer exchange from Phosphate buffer to Tris buffer (30 to 50 mM, pH: 7-7.5) with TFF system (100 kDa, 0.1 m$^2$) followed by addition of M-199 and 0.1-1.0% glycine.

In fourth aspect of the first embodiment purified virus pool in Tris buffer was subjected to inactivation by 0.01-1.0% formalin with continuous stirring of virus bulk and incubated at ambient temperature for 13 days, with intermediate filtration on day 7. Further, the inactivated bulk was subjected to final filtration and later stored at 2-8° C.

In fifth aspect of the first embodiment, final purified bulk was subjected to adsorption on Al(OH)3, wherein the final alum (Al$^{3+}$) concentration is between 0.1-1.5 mg/dose, M-199+0.5% glycine was used to make up the volume and pH was adjusted to 6-7 using 1N HCl/NaOH, further subjected to overnight stirring at 2-8° C.

The present inventors have surprisingly observed that D-antigen loss, post-formaldehyde inactivation was due to presence of phosphate buffer that unexpectedly causes undesirable aggregation of polio viruses. The instant invention provides an improved process of formaldehyde inactivation in presence of TRIS buffer thereby ensuring minimal epitopic modifications and subsequently minimizing D-antigen loss.

Inactivated Rotavirus:
Rotaviruses are the most common cause of severe diarrhoeal disease in young children throughout the world. Oral, live, attenuated rotavirus vaccines are available internationally; and are considered safe and effective in preventing gastrointestinal disease.

Second embodiment of the present invention comprises of preparation, purification and formulation of the rotavirus. The said process for preparation of Injectable heat Inactivated Rotavirus antigens having novel strain i.e. CDC-9 utilizes thermal inactivation and adsorption on aluminum hydroxide adjuvant.

In first aspect of the second embodiment, Rota virus was cultured using Vero cells (CCL-81) as host cells and the harvest was clarified using 30 μ and 2 μ filter assembly to remove cell debris.

In second aspect of the second embodiment, the clarified harvest was treated with Benzonase (2000-10000 units per liter) with incubation at 37° C. for 4 hours and continuous stirring. More particularly the concentration of benzonase used was 5000 units per liter.

In third aspect of the second embodiment, Benzonase treated bulk was further 10× concentrated and 4× diafiltered using 'HBSS (Hanks Balanced Salt Solution)+10% sorbitol' with 100 kDa cassettes.

In fourth aspect of the second embodiment, the diafiltered bulk can be optionally dialysed using a dilution buffer and further purified using affinity chromatography, preferably cellufine sulfate as a column chromatography resin.

In the fifth aspect of the second embodiment, an improved method of thermal inactivation of rotavirus was used. The method is rapid, simple, and can maintain the integrity and thereby preserve the antigenicity of Rotavirus particles. The temperature used for thermal inactivation was in range between 60° C. to 70° C.; and incubation time was in the range of about 10 minutes-24 hours, inclusive. Preferably the incubation time was in the range of about 30 minutes-10 hours. More preferably, inactivation of purified CDC-9 was done using heat at 60° C. for 5 hrs with one change of container after two hours. The inactivated CDC-9 bulk was stored at −80° C. until further use.

In sixth aspect of the second embodiment, adsorption of Inactivated Rotavirus antigen was done on Aluminum hydroxide, wherein the final Aluminum ($Al^{+++}$) concentration was between 0.2 mg/dose to 0.8 mg/dose.

Heamophillus influenzae b PRP-Protein Conjugate:

Haemophilus influenzae type b is a Gram-negative bacterium that causes meningitis and acute respiratory infections, mainly in children. The outermost structure of H. influenzae type b is composed of polyribosyl-ribitol-phosphate (PRP), a polysaccharide that is responsible for virulence and immunity. PRP is a hapten which is considered as poor immunogenic in nature hence PRP is linked covalently with a carrier protein to make highly immunogenic Hib antigen. This process changes the polysaccharide from a T-independent to a T-dependent antigen and greatly improves immunogenicity, particularly in young children.

Third embodiment of the present invention comprises of preparation of Hib PRP-protein conjugate. It may be noted that the carrier proteins used for the conjugation of the Hib antigen may be selected from group comprising of $CRM_{197}$ (Cross Reactive Material 197, a genetically detoxified form of diphtheria toxoid), Diphtheria toxoid, Neisseria meningitidis outer membrane complex, fragment C of tetanus toxoid, pertussis toxoid, protein D of H. influenzae, E. coli LT, E. coli ST, and exotoxin A from Pseudomonas aeruginosa, outer membrane complex c (OMPC), porins, transferrin binding proteins, pneumolysin, pneumococcal surface protein A (PspA), pneumococcal surface adhesin A (PsaA), pneumococcal PhtD, pneumococcal surface proteins BVH-3 and BVH-11 , protective antigen (PA) of Bacillus anthracis and detoxified edema factor (EF) and lethal factor (LF) of Bacillus anthracis, ovalbumin, keyhole limpet hemocyanin (KLH), human serum albumin, bovine serum albumin (BSA) and purified protein derivative of tuberculin (PPD), synthetic peptides, heat shock proteins, pertussis proteins, cytokines, lymphokines, hormones, growth factors, artificial proteins comprising multiple human CD4+ T cell epitopes from various pathogen-derived antigens such as N 19, iron-uptake proteins, toxin A or B from C. difficile and S.agalactiae proteins or any equivalents thereof. Preferably the carrier protein in conjugate is selected from TT or $CRM_{197}$.

In first aspects of the third embodiment, Hib antigen is derived from the capsular polysaccharide of Haemophilius influenzae type b strain. To produce the PRP polysaccharide, H. Influenzae type-b bacteria was grown in semi synthetic media under certain conditions of temperature, agitation and optical density etc. PRP is an outer membrane bound polysaccharide, gets released into the medium during the fermentation under agitation condition. Fermented biomass separated broth contains crude PRP, which was again purified by precipitation using a detergent N, N, N-trimethyl-l-hexadecanaminium bromide, followed by ethanol gradient precipitation and filtration. Final purified PRP polysaccharide was tested for meeting the specifications like endotoxin, nucleic acid and protein as per the WHO, BP, EP, IP etc.

In second aspect of the third embodiment, polysaccharide—protein conjugate was prepared by coupling of polysaccharide (PRP) with a carrier protein. Hib PRP was conjugated to carrier protein using conjugation process comprising of steps including depolymerization of PRP using alkaline buffer to achieve size reduced PRP; treatment with cyanylation agent like CDAP (1-cyano-4-dimethylamino pyridinium tetrafluoroborate) to form a cyanate ester; coupling of activated cyanylated polysaccharide to amino group of carrier protein; purification of final conjugate using ultrafiltration.

More preferably, the optimal input ratio of reactants i.e. PRP, CDAP and $CRM_{197}$ was selected at 1:1.5:1 ratio for conjugation reaction. During conjugation, purified PRP polysaccharide was depolymerized using an alkaline buffer (0.4 M Carb-Bicarbonate buffer, pH 10.5±0.1) to achieve size reduced PRP. Size reduced PRP was treated for cyanylation using CDAP (1-cyano-4-dimethylamino pyridinium tetrafluoroborate) chemistry to form a cyanate ester. The activated cyanylated polysaccharide was coupled directly with amino group on the carrier protein $CRM_{197}$. The degree of conversion of Hib conjugate was confirmed by the offline testing using HPLC. The conjugation reaction was quenched by achieving the desired level of conversion of conjugate with the specification of not less than 65% conversion of Hib conjugate, and then conjugate reaction was neutralized by Glycine (2M) addition. The Hib PRP-$CRM_{197}$ Conjugate was further purified on ultra filtration membrane filters (300 kDa and 100 kDa) to remove nonreactive reagents and byproducts. Final conjugate bulk is 0.22 µm filtered and stored at 2-8° C.

In third aspect of the third embodiment, Hib PRP is conjugated to carrier protein wherein the saccharide: protein ratio (w/w) is between 0.4 and 1;and the free PRP content in final Hib PRP—protein conjugate bulk is not more than 5%, more preferably is less than 2%.

Diphtheria toxoid (D)

Diphtheria is an infectious disease caused by the bacterium Corynebacterium diphtheria, which primarily infects the throat and upper airways, and produces a toxin affecting other organs. Diphtheria toxin is an exotoxin secreted by Corynebacterium diphtheria, possesses antigenic properties and is toxic in nature. To reduce toxicity, the toxin is converted to the inactive toxoid by subjecting it to inactivation. The inactivation process may be selected from one or more of treatment with Heat, UV, Formalin/Formaldehyde, Acetylethyleneimine, etc. To increase immunogenicity, the toxoid is adsorbed to an adjuvant. The toxoid thus formed is able to induce anti toxin antibodies against C diphtheria. Existence of dimers can lead to adverse reactions.

In fourth embodiment of the present invention, Diphtheria toxoid was prepared.

In first aspect of the fourth embodiment, diphtheria toxin (exotoxin) was obtained from Corynebacterium diphtheria and detoxified using a suitable inactivating agent. The example of suitable inactivating agent includes Formaldehyde.

In second aspect of the fourth embodiment, diphtheria toxoid obtained was purified using Gel filtration chromatography with Sephacryl S-300 HR as resin with linear flow rate of 2-5 ml/min The purified D thus obtained comprises of homogenous fraction devoid of undesirable aggregates (Refer FIG. 1) with at least 80-90% monomeric diphtheria toxoid further used for formulation of multivalent vaccine(s). Further PLgel, Sephacryl S-200HR, Sephadex, Bio-Gel (cross linked polyacrylamide), agarose gel and/or Styragel may also be used for the purpose of purification using Gel permeation chromatography.

In third aspect of the fourth embodiment, diphtheria toxoid was adsorbed on one or more of Aluminum salt including Aluminum hydroxide and Aluminum phosphate, preferably on Alum phosphate.

Tetanus toxoid (T)

Tetanus is an acute infectious disease caused by toxigenic strains of the bacterium Clostridium tetani (C. tetani), a gram-positive, spore-forming, strictly anaerobic bacterium. Tetanus toxin is an exotoxin secreted by Clostridium tetani, possesses antigenic properties and is toxic in nature. To reduce toxicity, the toxin is converted to the inactive toxoid by subjecting it to inactivation. The inactivation process may be selected from one or more of treatment with Heat, UV, Formalin/Formaldehyde, Acetylethyleneimine, etc. To increase immunogenicity, the toxoid is adsorbed to an adjuvant. The toxoid thus formed is able to induce anti toxin antibodies against Clostridium tetani. Existence of dimers can lead to adverse reactions.

In fifth embodiment of the present invention, Tetanus toxoid was prepared.

In first aspect of the fifth embodiment, Tetanus toxin was obtained from Clostridium tetani and detoxified using a suitable inactivating agent. The example of suitable inactivating agent includes Formaldehyde.

In second aspect of the fifth embodiment, Tetanus toxoid obtained was purified using Gel filtration chromatography with Sephacryl S-300 HR as resin with linear flow rate of 2-5 ml/min The purified T thus obtained was a homogenous fraction devoid of undesirable aggregates with at least 80-90% monomeric tetanus toxoid further used for formulation of multivalent vaccine. Further PLgel, Sephacryl S-200HR, Sephadex, Bio-Gel (cross-linked polyacrylamide), agarose gel and Styragel may also be used for the purpose of purification using Gel permeation chromatography.

In third aspect of the fourth embodiment, Tetanus toxoid was adsorbed on one or more of Aluminum salt including Aluminum hydroxide and Aluminum phosphate, preferably on Alum phosphate.

Pertussis Antigen

Pertussis (whooping cough) is caused by Bordetella pertussis, a small Gram-negative coccobacillus that infects the mucosal layers of the human respiratory tract. Two forms of vaccine are in use, the whole-cell pertussis vaccine (wP), and the acellular pertussis vaccine (aP). Whole-cell pertussis vaccines are suspensions of the entire B. pertussis organism that has been inactivated, usually with formalin Immunization with wP vaccine is relatively inexpensive and highly effective. Also, presence of wP in combination vaccines acts as an adjuvant for many other antigenic component.

Acellular pertussis (aP) vaccines contain purified components of B. pertussis such as inactivated pertussis toxin either alone or in combination with other B. pertussis components such as filamentous haemagglutinin, fimbrial antigens, pertactin, and modified adenylate cyclase. Acellular pertussis vaccine offers less adverse reaction as compared to wP vaccine.

In sixth embodiment of the present invention, the pertussis vaccine is pertussis antigen selected from one or more of whole cell pertussis or acellular pertussis.

In first aspect of the sixth embodiment, pertussis vaccine is an acellular pertussis antigen selected from one or more of filamentous haemagglutinin, fimbrial antigens, pertactin, and modified adenylate cyclase. Acellular pertussis antigens may be expressed in suitable host using recombinant DNA technology.

In second aspect of the sixth embodiment, pertussis vaccine is a whole cell pertussis comprising of Bordetella pertussis strains 134, 509, 25525 and 6229 in a specific ratio and subsequently inactivated by utilizing improved methods of inactivation devoid of thimerosal; hence leading to reduced reactogenicity and increased potency. Preferably, wP antigen is made from Bordetella pertussis strains 134, 509, 25525 and 6229 mixed in a ratio of 1:1:0.25:0.25.

In third aspect of the sixth embodiment, wP inactivation process includes heat inactivation at 56±2° C. for 10 to 15 minutes in presence of formaldehyde; wherein wP bulk remains non-clumpy and easily homogenized thereby leading to reduced reactogenicity and giving better wP potency for a longer duration.

Hepatitis B surface antigen (HBsAg)

Hepatitis B is a potentially life-threatening liver infection caused by the Hepatitis B virus (HBV). Hepatitis B surface antigen (HBsAg) is a surface protein that also acts as an immunogen in highly effective vaccines for prevention of HBV infection. HBsAg protein can be recombinantly expressed in a suitable host microorganism; or can be isolated from the blood plasma of a chronic Hepatitis B patient/carrier.

In seventh embodiment of the present invention, Hepatitis B surface antigen (HBsAg) was prepared.

In one of the aspect of seventh embodiment, HBsAg was expressed in Hansenula polymorpha yeast cells using recombinant DNA technology. Other yeasts such as Saccharomyces cerevisiae may also be used as host cell for recombinant expression of HBsAg.

In one of the aspect of seventh embodiment, Hepatitis B antigen (HBsAg) was adsorbed on one or more of Aluminum salt including Aluminum hydroxide and Aluminum phosphate, preferably on Alum phosphate.

Bivalent Combination Vaccine Composition and its Preparation Process

In eighth embodiment of the present invention, multivalent vaccine is an all liquid bivalent combination vaccine. The bivalent combination vaccine comprises of an inactivated polio virus of Type I, II and III; and Inactivated Rota virus (IRV).

In first aspect of the eighth embodiment, Inactivated polio virus is selected from the group of Salk and Sabin strain; and the concentration of individual Type 1, Type 2, and Type 3 of Salk or Sabin strain based IPV is not more than 20 D antigen units.

In second aspect of the eighth embodiment, inactivated polio virus is a Salk strain and the concentration of individual Type 1, Type 2, or Type 3 of Salk strain based IPV is selected from the group of dose composition comprising of 7.5-16-10, 8-2-5, 10-2-5, 10-2-10, 10-2-12, 10-2-16, 7.5-16-10, 5-2-5 D antigen units; more particularly concentration of individual Type 1, Type 2, or Type 3 of Salk strain based IPV is selected from group of 8-2-5 and 10-2-10 D antigen units.

In third aspect of the eighth embodiment, inactivated polio virus is a Sabin strain and the concentration of individual Type 1, Type 2, and Type 3 of Sabin strain based IPV is selected from the group of dose composition comprising of 5-16-10, 2.5-8-5, 5-8-10 D antigen units; more particularly concentration of individual Type 1, Type 2, and Type 3 of Sabin strain based IPV is 5-16-10 D antigen units.

In fourth aspect of the eighth embodiment, injectable heat inactivated rotavirus (IRV) is a Rotavirus CDC-9 or CDC-66 strain and the concentration of IRV is in the range of 5-50 μg/dose, more particularly the concentration of IRV is 10 μg/dose.

In fifth aspect of the eighth embodiment, bivalent composition was prepared by adsorbing IPV (Sabin/Salk strain) bulk and IRV bulk individually on one or more of Aluminum salt including Aluminum hydroxide and Aluminum phosphate, preferably on Alum hydroxide. The individual monovalent adsorbed bulks of IPV and IRV were further mixed together and kept on rocker at 2-8° C. for 1-4 hours.

Hexavalent Combination Vaccine Composition and its Preparation Process

In ninth embodiments of the present invention, all liquid Hexavalent (DTwP-IPV-IRV-Hib) vaccine formulation was prepared as follows:

a) IPV (Sabin/Salk strain) bulk and IRV bulk were individually adsorbed on Aluminum hydroxide, followed by pH adjustment to 6.2-6.6.
b) D was adsorbed on Aluminum phosphate, followed by pH adjustment to 5.5-6.5, addition of T and blending by agitation at room temperature for 18-24 hours.
c) The solutions obtained in step a and b were mixed, followed by pH adjustment to 6.4-6.6 and agitation at RT for 60 minutes.
d) wP antigen and Histidine were added to the above mixture, followed by agitation for 60 minutes and left in static condition for overnight at 2-8° C.
e) Hib PRP conjugate and 2-Phenoxyethanol (2-PE) were added to the mixture obtained in step d at 2-8 ° C., followed by pH adjustment to 6.4-6.6.
f) NaCl and WFI (q.s.) were added to the mixture obtained in step e, followed by agitation for 2 hours.

In tenth embodiment of the present invention, the multivalent vaccine composition is an all liquid hexavalent vaccine formulation. All liquid hexavalent vaccine formulation comprises of Diphtheria toxoid (D); Tetanus toxoid (T); Inactivated whole cell B. pertussis antigen (wP); Inactivated polio virus salk strains of Type I, II and III; Inactivated Rota virus (IRV); and H. influenzae type b PRP-TT conjugate and other excipients like Aluminum based adjuvant (Aluminum phosphate, Aluminum hydroxide), 2-phenoxyethanol, L-Histidine and WFI.

In one of the preferred aspect of the tenth embodiment, the multivalent vaccine composition is an hexavalent vaccine composition wherein D is present in an amount in the range of 1-50 Lf; T is present in an amount in the range of 1-30 Lf; wP is present in an amount in the range of 10-50 IOU; Dose reduced inactivated Salk strain of polio virus type 1 is present in an amount in the range of 1-20 D antigen units, type 2 in the range of 1-20 D antigen units, Type 3 in the range of 1-20 D antigen units; IRV is present in an amount in the range of 1-30 μg; H. influenzae type b PRP-TT conjugate is in an amount in the range of 2-20 μg of PRP content; aluminum content ($Al^{3+}$) is present in an amount in range of 0.4-1.5 mg; 2-Phenoxyethanol is present in an amount in the range of 2-6 mg; L-Histidine is present in the range of 0.5-5 mg and WFI.

In one of the most preferred aspect of the tenth embodiment, the multivalent vaccine composition is an hexavalent vaccine composition wherein D is present in an amount 22.5 Lf; TT is present in an amount 7.5 Lf; wP is present in an amount 15 IOU; Dose reduced inactivated Salk strain of polio virus type 1 is present in an amount 10 D units, type 2 is present in an amount 2 D units, Type 3 is present in an amount 10 or 16 D units; IRV is present in an amount 10 μg; influenzae type b PRP-TT conjugate is in an amount 5 ; Aluminum content is present in an amount not more than 0.9 mg; 2-Phenoxyethanol is present in an amount 3.25 mg; L-Histidine is present in the amount of 1.55 mg and WFI.

In eleventh embodiments of the present invention, the multivalent vaccine composition is an all liquid hexavalent vaccine formulation. All liquid hexavalent vaccine formulation comprises of Diphtheria toxoid (D); Tetanus toxoid (T); Inactivated whole cell B. pertussis antigen (wP); Inactivated polio virus salk strains of Type I, II and III; Inactivated Rota virus (IRV); and H. influenzae type b PRP-$CRM_{197}$ conjugate and other excipients like Aluminum based adjuvant (Aluminum phosphate, Aluminum hydroxide), 2-phenoxyethanol, L-Histidine and WFI.

In one of the preferred aspect of the eleventh embodiment, the multivalent vaccine composition is an hexavalent vaccine composition wherein D is present in an amount in the range of 1-50 Lf; T is present in an amount in the range of 1-30 Lf; wP is present in an amount in the range of 10-50 IOU; Dose reduced inactivated Salk strain of polio virus type 1 is present in an amount in the range of 1-20 D units, type 2 in the range of 1-20 D units, Type 3 in the range of 1-20 D units; IRV is present in an amount in the range of 1-30 μg; H. influenzae type b PRP- $CRM_{197}$ conjugate is in an amount in the range of 2-20 μg of PRP content; aluminum content ($Al^{3+}$) is present in an amount in range of 0.4-1.5 mg; 2-Phenoxyethanol is present in an amount in the range of 2-6 mg; L-Histidine is present in the range of 0.5-5 mg and WFI.

In one of the most preferred aspect of the eleventh embodiment, the multivalent vaccine composition is an hexavalent vaccine composition wherein D is present in an amount 22.5 Lf; T is present in an amount 7.5 Lf; wP is present in an amount 15 IOU; Dose reduced inactivated Salk strain of polio virus type 1 is present in an amount 10 D units, type 2 is present in an amount 2 D units, Type 3 is present in an amount 10 or 16 D units; IRV is present in an amount 10 μg; H influenzae type b PRP-CRM197 conjugate is in an amount 10 μg; Aluminum content is present in an amount not more than 0.9 mg; 2-Phenoxyethanol is present in an amount 3.25 mg; L-Histidine is present in the range of 1.55 mg and WFI.

In twelfth embodiments of the present invention, the multivalent vaccine composition is an all liquid hexavalent vaccine formulation. All liquid hexavalent vaccine formulation comprises of Diphtheria toxoid (D); Tetanus toxoid (T); Inactivated whole cell B. pertussis antigen (wP); Inactivated polio virus sabin strains of Type I, II and III; Inactivated Rota virus (IRV); and H. influenzae type b PRP-TT conjugate and other excipients like Aluminum based adjuvant (Aluminum phosphate, Aluminum hydroxide), 2-phenoxyethanol, L-Histidine and WFI.

In one of the preferred aspect of the twelfth embodiment, the multivalent vaccine composition is an hexavalent vaccine composition wherein D is present in an amount in the range of 1-50 Lf; T is present in an amount in the range of 1-30 Lf; wP is present in an amount in the range of 10-50 IOU; Dose reduced inactivated sabin strain of polio virus type 1 is present in an amount in the range of 1-20 D antigen units, type 2 in the range of 1-20 D antigen units, Type 3 in the range of 1-20 D antigen units; IRV is present in an amount in the range of 1-30 µg; H. influenzae type b PRP-TT conjugate is in an amount in the range of 2-20 µg of PRP content; aluminum content ($Al^{3+}$) is present in an amount in range of 0.4-1.5 mg; 2-Phenoxyethanol is present in an amount in the range of 2-6 mg; L-Histidine is present in the range of 0.5-5 mg and WFI.

In one of the most preferred aspect of the twelfth embodiment, the multivalent vaccine composition is an hexavalent vaccine composition wherein D is present in an amount 22.5 Lf; T is present in an amount 7.5 Lf; wP is present in an amount 15 IOU; Dose reduced inactivated sabin strain of polio virus type 1 is present in an amount 5 D units, type 2 is present in an amount 16 D units, Type 3 is present in an amount 10 D units; IRV is present in an amount 10 µg; influenzae type b PRP-TT conjugate is in an amount 5 µg; Aluminum content is present in an amount not more than 0.9 mg; 2-Phenoxyethanol is present in an amount 3.25 mg; L-Histidine is present in the range of 1.55 mg and WFI.

In thirteenth embodiments of the present invention, the multivalent vaccine composition is a all liquid hexavalent vaccine formulation. All liquid hexavalent vaccine formulation comprises of Diphtheria toxoid (D); Tetanus toxoid (T); Inactivated whole cell B. pertussis antigen (wP); Inactivated polio virus sabin strains of Type I, II and III; Inactivated Rota virus (IRV); and H. influenzae type b PRP-$CRM_{197}$ conjugate and other excipients like Aluminum based adjuvant (Aluminum phosphate, Aluminum hydroxide), 2-phenoxyethanol, L-Histidine and WFI.

In one of the preferred aspect of the thirteenth embodiment, the multivalent vaccine composition is an hexavalent vaccine composition wherein D is present in an amount in the range of 1-50 Lf; T is present in an amount in the range of 1-30 Lf; wP is present in an amount in the range of 10-50 IOU; Dose reduced inactivated sabin strain of polio virus type 1 is present in an amount in the range of 1-20 D antigen units, type 2 in the range of 1-20 D antigen units, Type 3 in the range of 1-20 D antigen units; IRV is present in an amount in the range of 1-30 µg; H. influenzae type b PRP-$CRM_{197}$ conjugate is in an amount in the range of 2-20 µg of PRP content; aluminum content ($Al^{3+}$) is present in an amount in range of 0.4-1.5 mg; 2-Phenoxyethanol is present in an amount in the range of 2-6 mg; L-Histidine is present in the range of 0.5-5 mg and WFI.

In one of the most preferred aspect of the thirteenth embodiment, the multivalent vaccine composition is an hexavalent vaccine composition wherein D is present in an amount 22.5 Lf; T is present in an amount 7.5 Lf; wP is present in an amount 15 IOU; Dose reduced inactivated sabin strain of polio virus type 1 is present in an amount 5 D units, type 2 is present in an amount 16 D units, Type 3 is present in an amount 10 D units; IRV is present in an amount 10 µg; influenzae type b PRP-$CRM_{197}$ conjugate is in an amount 10 µg; Aluminum content is present in an amount not more than 0.9 mg; 2-Phenoxyethanol is present in an amount 3.25 mg; L-Histidine is present in the range of 1.55 mg and WFI.

Heptavalent Combination Vaccine Composition and its Preparation Process

In fourteenth embodiment of the present invention, Heptavalent (DTwP-HBsAg-IPV-IRV-Hib) vaccine formulation was prepared as follows:
a) IPV (Sabin/Salk strain) bulk and IRV bulk were individually adsorbed on Aluminum hydroxide, followed by pH adjustment to 6.2-6.6.
b) HBsAg was adsorbed on Aluminum phosphate, followed by pH adjustment to 6.0-6.5.
c) D was adsorbed on Aluminum phosphate, followed by pH adjustment to 5.5-6.5 and addition of T.
d) Solution obtained in step b and c, followed by blending agitation at room temperature for 18-24 hours.
e) Above mixtures [as obtained in step a and d] were added, followed by pH adjustment to 6.4-6.6 and agitation at RT for 60 minutes.
f) wP antigen and Histidine were added to the above mixture, followed by agitation for 60 minutes and left in static condition for overnight at 2-8° C.
g) Hib PRP protein conjugate and 2-PE were added to the mixture obtained in step f at 2-8° C., followed by pH adjustment to 6.4-6.6.
h) NaCl and WFI (q.s.) were added to the mixture obtained in step g, followed by agitation for 2 hours.

In fifteenth embodiment of the present invention, the multivalent vaccine composition is a all liquid heptavalent vaccine formulation. All liquid heptavalent vaccine formulation comprises of Diphtheria toxoid (D); Tetanus toxoid (T); Inactivated whole cell B. pertussis antigen (wP); Inactivated polio virus salk strains of Type I, II and III; Inactivated Rota virus (IRV); and H. influenzae type b PRP-TT conjugate; Hepatitis B surface antigen (HBsAg) and other excipients like Aluminum based adjuvant (Aluminum phosphate, Aluminum hydroxide), 2-phenoxyethanol, L-Histidine and WFI.

In one of the preferred aspect of the fifteenth embodiment, the multivalent vaccine composition is an heptavalent vaccine composition wherein D is present in an amount in the range of 1-50 Lf; T is present in an amount in the range of 1-30 Lf; wP is present in an amount in the range of 10-50 IOU; Dose reduced inactivated Salk strain of polio virus type 1 is present in an amount in the range of 1-20 D antigen units, type 2 in the range of 1-20 D antigen units, Type 3 in the range of 1-20 D antigen units; IRV is present in an amount in the range of 1-30 µg; H. influenzae type b PRP-TT conjugate is present in an amount in the range of 2-20 µg of PRP content; Hepatitis B surface antigen (HBsAg) is present in an amount in the range of 5-30 µg; aluminum content ($Al^{3+}$) is present in an amount in range of 0.4-1.5 mg; 2-Phenoxyethanol is present in an amount in the range of 2-6 mg; L-Histidine is present in the range of 0.5-5 mg and WFI.

In one of the most preferred aspect of the fifteenth embodiment, the multivalent vaccine composition is an heptavalent vaccine composition wherein D is present in an amount 22.5 Lf; T is present in an amount 7.5 Lf; wP is present in an amount 15 IOU; Dose reduced inactivated Salk strain of polio virus type 1 is present in an amount 10 D units, type 2 is present in an amount 2 D units, Type 3 is present in an amount 10 or 16 D units; IRV is present in an amount 10 µg; influenzae type b PRP-TT conjugate is in an amount 5 µg; Hepatitis B surface antigen (HBsAg) is present in an amount 12.5 µg; Aluminum content is present in an amount not more than 0.9 mg; 2-Phenoxyethanol is present in an amount 3.25 mg; L-Histidine is present in the range of 1.55 mg and WFI.

In sixteenth embodiment of the present invention, the multivalent vaccine composition is an all liquid heptavalent vaccine formulation. All liquid heptavalent vaccine formulation comprises of Diphtheria toxoid (D); Tetanus toxoid (T); Inactivated whole cell B. pertussis antigen (wP); Inactivated polio virus salk strains of Type I, II and III; Inactivated Rota virus (IRV); and H. influenzae type b PRP-$CRM_{197}$ conjugate; Hepatitis B surface antigen (HBsAg)

and other excipients like Aluminum based adjuvant (Aluminum phosphate, Aluminum hydroxide), 2-phenoxyethanol, L-Histidine and WFI.

In one of the preferred aspect of the sixteenth embodiment, the multivalent vaccine composition is an heptavalent vaccine composition wherein D is present in an amount in the range of 1-50 Lf; T is present in an amount in the range of 1-30 Lf; wP is present in an amount in the range of 10-50 IOU; Dose reduced inactivated Salk strain of polio virus type 1 is present in an amount in the range of 1-20 D antigen units, type 2 in the range of 1-20 D antigen units, Type 3 in the range of 1-20 D antigen units; IRV is present in an amount in the range of 1-30 μg; H. influenzae type b PRP-$CRM_{197}$ conjugate is in an amount in the range of 2-20 μg of PRP content; Hepatitis B surface antigen (HBsAg) is present in an amount in the range of 5-30 μg; aluminum content ($Al^{3+}$) is present in an amount in range of 0.4-1.5 mg; 2-Phenoxyethanol is present in an amount in the range of 2-6 mg; L-Histidine is present in the range of 0.5-5 mg and WFI.

In one of the most preferred aspect of the sixteenth embodiment, the multivalent vaccine composition is an heptavalent vaccine composition wherein D is present in an amount 22.5 Lf; T is present in an amount 7.5 Lf; wP is present in an amount 15 IOU; Dose reduced inactivated Salk strain of polio virus type 1 is present in an amount 10 D units, type 2 is present in an amount 2 D units, Type 3 is present in an amount 10 or 16 D units; IRV is present in an amount 10 μg; influenzae type b PRP-$CRM_{197}$ conjugate is in an amount 10 μg of PRP content; Hepatitis B surface antigen (HBsAg) is present in an amount 12.5 μg; Aluminum content is present in an amount not more than 0.9 mg; 2-Phenoxyethanol is present in an amount 3.25 mg; L-Histidine is present in the range of 1.55 mg and WFI.

In seventeenth embodiments of the present invention, the multivalent vaccine composition is a all liquid heptavalent vaccine formulation. All liquid heptavalent vaccine formulation comprises of Diphtheria toxoid (D); Tetanus toxoid (T); Inactivated whole cell B. pertussis antigen (wP); Inactivated polio virus sabin strains of Type I, II and III; Inactivated Rota virus (IRV); and H. influenzae type b PRP-TT conjugate; Hepatitis B surface antigen (HBsAg) and other excipients like Aluminum based adjuvant (Aluminum phosphate, Aluminum hydroxide), 2-phenoxyethanol, L-Histidine and WFI.

In one of the preferred aspect of the seventeenth embodiment, the multivalent vaccine composition is an heptavalent vaccine composition wherein D is present in an amount in the range of 1-50 Lf; T is present in an amount in the range of 1-30 Lf; wP is present in an amount in the range of 10-50 IOU; Dose reduced inactivated sabin strain of polio virus type 1 is present in an amount in the range of 1-20 D units, type 2 in the range of 1-20 D units, Type 3 in the range of 1-20 D units; IRV is present in an amount in the range of 1-30 μg; H. influenzae type b PRP-TT conjugate is in an amount in the range of 2-20 μg of PRP content; Hepatitis B surface antigen (HBsAg) is present in an amount in the range of 5-30 μg; aluminum content ($Al^{3+}$) is present in an amount in range of 0.4-1.5 mg; 2-Phenoxyethanol is present in an amount in the range of 2-6 mg; L-Histidine is present in the range of 0.5-5 mg and WFI.

In one of the most preferred aspect of the seventeenth embodiment, the multivalent vaccine composition is an heptavalent vaccine composition wherein D is present in an amount 22.5 Lf; T is present in an amount 7.5 Lf; wP is present in an amount 15 IOU; Dose reduced inactivated sabin strain of polio virus type 1 is present in an amount 5 D units, type 2 is present in an amount 16 D units, Type 3 is present in an amount 10 D units; IRV is present in an amount 10 μg; H. influenzae type b PRP-TT conjugate is in an amount 5 μg of PRP content; Hepatitis B surface antigen (HBsAg) is present in an amount 12.5 μg; Aluminum content is present in an amount not more than 0.9 mg; 2-Phenoxyethanol is present in an amount 3.25 mg; L-Histidine is present in the range of 1.55 mg and WFI.

In eighteenth embodiments of the present invention, the multivalent vaccine composition is a all liquid heptavalent vaccine formulation. All liquid heptavalent vaccine formulation comprises of Diphtheria toxoid (D); Tetanus toxoid (T); Inactivated whole cell B. pertussis antigen (wP); Inactivated polio virus sabin strains of Type I, II and III; Inactivated Rota virus (IRV); H. influenzae type b PRP-$CRM_{197}$ conjugate; Hepatitis B surface antigen (HBsAg) and other excipients like Aluminum based adjuvant (Aluminum phosphate, Aluminum hydroxide), 2-phenoxyethanol, L-Histidine and WFI.

In one of the preferred aspect of the eighteenth embodiment, the multivalent vaccine composition is an heptavalent vaccine composition wherein D is present in an amount in the range of 1-50 Lf; T is present in an amount in the range of 1-30 Lf; wP is present in an amount in the range of 10-50 IOU; Dose reduced inactivated sabin strain of polio virus type 1 is present in an amount in the range of 1-20 D antigen units, type 2 in the range of 1-20 D antigen units, Type 3 in the range of 1-20 D antigen units; IRV is present in an amount in the range of 1-30 μg; H. influenzae type b PRP-$CRM_{197}$ conjugate is in an amount in the range of 2-20 μg of PRP content; Hepatitis B surface antigen (HBsAg) is present in an amount in the range of 5-30 μg; aluminum content ($A^{3+}$) is present in an amount in range of 0.4-1.5 mg; 2-Phenoxyethanol is present in an amount in the range of 2-6 mg; L-Histidine is present in the range of 0.5-5 mg and WFI.

In one of the most preferred aspect of the eighteenth embodiment, the multivalent vaccine composition is an heptavalent vaccine composition wherein D is present in an amount 22.5 Lf; T is present in an amount 7.5 Lf; wP is present in an amount 15 IOU; Dose reduced inactivated sabin strain of polio virus type 1 is present in an amount 5 D antigen units, type 2 is present in an amount 16 D antigen units, Type 3 is present in an amount 10 D antigen units; IRV is present in an amount 10 μg; influenzae type b PRP-$CRM_{197}$ conjugate is in an amount 10 μg of PRP content; Hepatitis B surface antigen (HBsAg) is present in an amount 12.5 μg; Aluminum content is present in an amount not more than 0.9 mg; 2-Phenoxyethanol is present in an amount 3.25 mg; L-Histidine is present in the range of 1.55 mg and WFI.

In nineteenth embodiment of the present invention, the combination vaccine composition/formulation comprises of one or more preservative selected from the group consisting of Benzethonium chloride (Phemerol), thiomersal, Phenol and 2- phenoxyethanol (2-PE). More preferably, the combination vaccine composition/formulation comprise of 2-phenoxyethanol (2-PE) as preservative.

In twentieth embodiment of the present invention, the combination vaccine composition/formulation contain one or more pharmaceutically acceptable excipients selected from the group consisting of sugars and polyols, surfactants, polymers, salts, aminoacids, pH modifiers, etc.

In first aspect of the twentieth embodiment, sugars and polyols includes sucrose, trehalose, lactose, maltose, galactose, mannitol, sorbitol, glycerol, etc. In second aspect of the twentieth embodiment, surfactants include non-ionic surfactants such as polysorbate 20, polysorbate 80, etc. In third aspect of the twentieth embodiment polymers include dextran, carboxymethylcellulose, hyaluronic acid, cyclodextrin, etc. Examples of the salts may include NaCl, $MgCl_2$, KCl, $CaCl_2$, etc. In fourth aspect of the twentieth embodiment amino acids includes Arginine, Glycine, Histidine, etc. In fifth aspect of the twentieth embodiment pH modifiers includes sodium hydroxide, hydrochloric acid, etc.

In twenty-first embodiment of the present invention, the pH of the final combination vaccine composition/formulation is in the range of pH 6.0 to pH 7.5; more preferably in the range of pH 6.2 to pH 7.2; and most preferably in the range of pH 6.4 to pH 6.6.

EXAMPLES

Example 1

Preparation of Dose Reduced Inactivated Polio Virus (Salk/Sabin) antigen

Serum Institute of India has developed inactivation and adsorption of Inactivated polio virus as per following protocol:

CCL81-VERO (Monkey kidney) cell were used as host cells for the growing of polio viruses i.e. sabin and salk strains.

Purification of IPV

Clarified harvest pool was concentrated to 10× using tangential flow filtration system with 100 KDa cassettes (0.5 m²) and then diafiltered 3 times of harvest volume with phosphate buffer (40 mM, pH : 7.0)

The concentrate was purified by Ion Exchange Chromatography (IEC). 10× TFF concentrate was passed through DEAE Sepharose fast flow (Weak-Anion exchanger) packed in column xk-26 using Akta explorer (GE Healthcare). Negatively charged impurities were bound to the column whereas polio virus was collected in flow through with phosphate buffer 40 mM.

To minimize the loss of antigen in a quite cumbersome inactivation procedure (13 days), purified virus pool was buffer exchanged from phosphate buffer to TRIS buffer (40 mM, pH:7) with TFF system [100 KDa ,0.1 m2). The purified virus pool was exchanged with three volumes of tris buffer.

Inactivation of IPV

10× concentrated M-199 with 0.5% glycine were added so as to achieve final concentration 1×. Inactivation agent formalin (0.025%) was added into purified virus bulk while constant mixing. Inactivation was carried out at 37° C. while continuous stirring for 13 days containing 0.22 u filtration on 7th day and 13th day.

Result and Conclusion

When formaldehyde inactivation methods were particularly carried out in presence of phosphate buffer, significant D-antigen losses were observed for Sabin and Salk strains, whereas it was found that formaldehyde inactivation in presence of TRIS buffer resulted in minimum loss of D-antigen.

| | D - antigen content (40 mM Phosphate buffer during inactivation) | D - antigen content (40 mM Tris buffer during inactivation) |
|---|---|---|
| Type I | 52.70 DU/ml | 408.19 DU/ml |
| Type II | 22.63 DU/ml | 180.20 DU/ml |
| Type III | 4.21 DU/ml | 21.50 DU/ml |

Example 2

Preparation of Injectable heat Inactivated Rotavirus (IRV) antigen

Rotavirus strain (CDC-9) as disclosed in PCT Patent Application No. PCT/US2010/034537 entitled "New Human Rotavirus Strains and Vaccines", filed May 12, 2010; PCT Patent Application No. PCT/US2008/075239 entitled "Thermal Inactivation of Rotavirus", filed Sep. 4, 2008 was used.

Centers for Disease Control and Prevention (CDC) has developed a method for rotavirus inactivation. CDC has also developed assay for testing rotavirus specific IgG and neutralizing Antibodies.

Rota virus (CDC-9 strain) was cultured using Vero cells (CCL-81) as host cells and the harvest was clarified using 30+2 µ filter to remove cell debris.

The clarified harvest was treated with Benzonase (5000 units per litre) with incubation at 37° C. for 4 hours with continuous stirring.

Benzonase treated bulk was further 10× concentrate and 4× diafiltered using 'HBSS (Hanks Balanced Salt Solution) +10% sorbitol' with 100 KDa cassettes.

The diafiltered bulk was dialysed using a dilution buffer and was further purified using affinity chromatography (cellufine sulfate resin).

Inactivatin of purified CDC-9 was done using heat at 60° C. for 5 hrs with one change of container after two hours. The inactivated CDC-9 bulk was stored at −80° C. until further use. [Serum 1]

Example 3

Purification of Diphtheria toxoid

Diphtheria toxoid was purified using Gel filtration chromatography with process parameters set as below:

TABLE 1

| Process Parameters | | |
|---|---|---|
| Sr. No. | Parameter | Details |
| 1 | Used Native Bulk D | — |
| 2 | Content (Native Bulk D) by Lowry's assay | 11 mg/ml |
| 3 | LF/ml | 3000 |
| 4 | Method of Purification | Gel Filtration Chromatography (GFC) |
| 5 | Resin | Sephacryl S-300 HR |
| 6 | Column Used | XK 26/70 cm |
| 7 | Column Packed bed height | ~50 cm |
| 8 | Linear Flow rate | 1-3 ml/min |
| 9 | Sample (D) loading | 4% of total bed volume |
| 10 | Fraction Collection | 5 ml each (2 min) |
| 11 | Analysis | Lowry's assay, LF estimation, % Monomer |

Fractions no 6 to 11 were pooled and analyzed for monomer content. (Refer FIG. 1).

Results & Interpretation:

Multiple runs were performed using above same parameters. $CRM_{197}$ bulk concentrate was used as a marker to compare % monomer content. Monomeric $CRM_{197}$ can be considered purest form of DT. The percent monomer content was found to be in the range of 80-90%.

TABLE 2

% Recovery & Monomer content of purified DT obtained

| Sr. No. | Sample | Protein Conc. (mg/mL) | % Monomer | % Recovery |
|---|---|---|---|---|
| 1 | Native DT | — | 67.19 | — |
| 2 | Native CRM | — | 86.96 | — |
| 3 | GFC DT FR 8 | 2.03 | 83.21 | Injected DT Qty 120 mg Obtained Qty 75.1 mg (62.5%) |
| 4 | GFC DT FR 9 | 3.38 | 87.15 | |
| 5 | GFC DT FR 10 | 4.08 | 87.24 | |
| 6 | GFC DT FR 11 | 3.52 | 86.60 | |
| 7 | GFC DT FR 12 | 2.01 | 89.97 | |
| 8 | GFC DT FR 10-11 | 3.83 | 86.03 | 31.6% |
| 9 | GFC DT FR 9-12 | 2.96 | 87.42 | 48.9% |
| 10 | GFC DT FR 7-13 | 2.19 | 86.24 | 63.3% |

Example 4

Purification of Tetanus Toxoid

Tetanus toxoid was purified using Gel filtration chromatography/HIC (Phenyl Sepharose) with process parameters set as below:

TABLE 3

Process Parameters

| Sr. No. | Parameter | Details |
|---|---|---|
| 1 | Used Native Bulk T | — |
| 2 | Content (Native Bulk T) by Lowry's assay | 11 mg/ml |
| 3 | LF/ml | 3000 |
| 4 | Method of Purification | Gel Filtration Chromatography (GFC) |
| 5 | Resin | Sephacryl S-300 HR |
| 6 | Column Used | XK 26/70 cm |
| 7 | Column Packed bed height | ~50 cm |

TABLE 3-continued

Process Parameters

| Sr. No. | Parameter | Details |
|---|---|---|
| 8 | Linear Flow rate | 1-3 ml/min |
| 9 | Sample (T) loading | 4% of total bed volume |
| 10 | Fraction Collection | 5 ml each (2 min) |
| 11 | Analysis | Lowry's assay, LF estimation, % Monomer |

Results:

Multiple runs were performed using above same parameters. The percent monomer content was found to be in the range of 80-90%.

Example 5

Preparation of Hib PRP-Protein conjugate

PRP polysaccharide was produced as follows:

H. Influenzae type-b bacteria was grown in semi synthetic media under certain conditions of temperature, agitation and optical density etc. PRP is an outer membrane bound polysaccharide, gets released into the medium during the fermentation under agitation condition. Fermented biomass separated broth contains crude PRP, which is again purified by precipitation using a detergent N, N, N-trimethyl-1-hexadecanaminium bromide, followed by ethanol gradient precipitation and filtration. Final purified PRP polysaccharide was tested for meeting the specifications like endotoxin, nucleic acid and protein as per the WHO, BP, EP, IP etc.

Hib PRP-protein conjugate was prepared as follows:

The polysaccharide conjugate was prepared by coupling of PRP polysaccharide with a $CRM_{197}$ carrier protein. The input ratio of reactants i.e. PRP polysaccharide, CDAP and $CRM_{197}$ was selected at 1:1.5:1 ratio for conjugation reaction. During conjugation, purified PRP polysaccharide was depolymerized using an alkaline buffer (0.4M Carb-Bicarbonate buffer, pH 10.5±0.1) to achieve size reduced PRP. Size reduced PRP is treated for cyanylation using CDAP (1-cyano-4-dimethylamino pyridinium tetrafluoroborate) chemistry to form a cyanate ester. The activated cyanylated polysaccharide may thus be coupled directly with amino group on the carrier protein $CRM_{197}$. The degree of conversion of Hib conjugate was confirmed by the HPLC. The conjugation reaction was quenched by achieving the desired level of conversion of conjugate with the specification of not less than 65% conversion of Hib conjugate, and then conjugate reaction was neutralized by Glycine (2M) addition. The Hib PRP-$CRM_{197}$ Conjugate is purified on ultra filtration membrane filters (300 kDa and 100 kDa) to remove nonreactive reagents and by-products. Final conjugate bulk was 0.22 µm filtered and stored at 2-8° C.

Quality characteristics of Hib PRP-$CRM_{197}$ conjugate antigen obtained were as follow:

PRP content (mg/mL) : 1.49

Protein content (mg/mL): 2.98

Ratio (Ps : Protein) : 0.52

Free PRP (%) : 1.77

PMW (1(D) : 983

Avg MW (kD) : 752

Example 6

Composition of Bivalent (IPV-IRV vaccine)

Serum Institute of India has developed bivalent composition comprising dose reduced inactivated polio virus and Inactivated Rotavirus as per following protocol:

Composition of the bivalent vaccine is as under

TABLE 4

| | Bivalent Composition | | | |
|---|---|---|---|---|
| Components | Bivalent Vaccine Composition I (Salk IPV + IRV) | Bivalent Vaccine Composition II (Salk IPV + IRV) | Bivalent Vaccine Composition III (Salk IPV + IRV) | Bivalent Vaccine Composition IV (Sabin IPV + IRV) |
| Antigen content - IPV | Type 1: ≥8 DU/dose Type 2: ≥2 DU/dose Type 3: ≥5 DU/dose | Type 1: ≥10 DU/dose Type 2: ≥2 DU/dose Type 3: ≥10 DU/dose | Type 1: ≥10 DU/dose Type 2: ≥2 DU/dose Type 3: ≥16 DU/dose | Type 1: ≥5DU/dose Type 2: ≥16DU/dose Type 3: ≥10DU/dose |
| Antigen content - IRV | Total Protein ≥10 mcg/dose | Total Protein ≥10 mcg/dose | Total Protein ≥10 mcg/dose | Total Protein ≥10 mcg/dose |
| Alum | 0.8 mg/dose | 0.8 mg/dose | 0.8 mg/dose | 0.8 mg/dose |

Example 7

Preparation of Bivalent (IPV-IRV) vaccine

The bivalent (IPV-IRV) vaccine was prepared as per below procedure:

Adsorption of IPV
- Take desired volume of Al (OH)3 in a vessel.
- Add desired volume of monovalent Salk/Sabin IPV bulk and make final volume with diluent.
- Adjust the final formulation pH to 6.5 with 1 N NaOH/1N HCl.
- Keep the monovalent formulation bulks on magnetic stirrer/rocker overnight at 2-8° C.

Adsorption of IRV
- Take desired volume of Al (OH)3 in a vessel.
- Add desired volume of IRV bulk and make final volume with diluents.
- Adjust the final formulation pH to 6.5 with 1 N NaOH/1N HCl.
- Keep the monovalent formulation bulks on magnetic stirrer/rocker overnight at 2-8° C.

Formulation of Bivalent (IPV-IRV) Vaccine
- Mix the monovalent bulks of IPV and IRV formulations.
- Keep at 2-8° C. on rocker for 2 Hrs.
- Store the final formulation at 2-8° C. until further use.

Example 8

Efficacy Testing of Bivalent Vaccine

Potency of bivalent vaccine was examined by testing serum samples for neutralizing antibody against polio virus Sabin type 1, 2, and 3, as well as rotavirus strain Wa using microneutralization assays. Neutralization titers against polio viruses are reported in log2 format. A neutralization titer of 2.5 is considered negative. For rotavirus, a neutralization titer <20 is considered negative.

TABLE 5

| Sample | ID | Sabin 1 D 0 | Sabin 1 D 42 | Sabin 2 D 0 | Sabin 2 D 42 | Sabin 3 D 0 | Sabin 3 D 42 | IRV (Wa) D 0 | IRV (Wa) D 42 |
|---|---|---|---|---|---|---|---|---|---|
| Salk 8-2-5 + IRV 10 ug | 7A | 2.5 | 6.17 | 2.5 | 10.5 | 2.5 | 7.83 | <20 | 320 |
| | 7B | 2.5 | 4.5 | 2.5 | 7.17 | 2.5 | 2.5 | <20 | 1280 |
| | 8A | 2.5 | 7.83 | 2.5 | 9.5 | 2.5 | 8.83 | <20 | 320 |
| | 8B | 2.5 | 8.5 | 2.5 | 10.5 | 2.5 | 6.5 | <20 | 160 |
| Salk 5-2-5 + IRV 10 ug | 9A | 2.5 | 5.5 | 2.5 | 10.5 | 2.5 | 3.5 | <20 | 640 |
| | 9B | 2.5 | 2.5 | 2.5 | 8.83 | 2.5 | 5.83 | <20 | 640 |
| Sabin 5-16-10 + IRV 10 ug | 10A | 2.5 | 7.5 | 2.5 | 9.5 | 2.5 | 6.5 | <20 | 640 |
| | 10B | 2.5 | 10.5 | 2.5 | 10.5 | 2.5 | 10.5 | <20 | 320 |
| | 11A | 2.5 | 10.5 | 2.5 | 10.5 | 2.5 | 10.5 | <20 | 640 |
| | 11B | 2.5 | 10.5 | 2.5 | 10.5 | 2.5 | 9.17 | <20 | 640 |
| Sabin 2.5-8-5 + IRV 10 ug | 12A | 2.5 | 10.5 | 2.5 | 10.5 | 2.5 | 8.83 | <20 | 320 |
| | 12B | 2.5 | 10.5 | 2.5 | 10.5 | 2.5 | 8.17 | <20 | 80 |
| Rota Live (Log 5.5 FFU) | 15A | 2.5 | 2.5 | 2.5 | 2.5 | 2.5 | 2.5 | <20 | 320 |
| | 15B | 2.5 | 2.5 | 2.5 | 2.5 | 2.5 | 2.5 | <20 | 640 |
| Negative | 17A | 2.5 | 2.5 | 2.5 | 2.5 | 2.5 | 2.5 | <20 | <20 |
| | 17B | 2.5 | 2.5 | 2.5 | 2.5 | 2.5 | 2.5 | <20 | <20 |
| | controls | 6.5 | | 4.83 | | 4.17 | | <20 | |

TABLE 5-continued

| Sample ID | Sabin 1 | | Sabin 2 | | Sabin 3 | | IRV (Wa) | |
|---|---|---|---|---|---|---|---|---|
| | D 0 | D 42 | D 0 | D 42 | D 0 | D 42 | D 0 | D 42 |
| | | 6.5 | | 5.17 | | 4.5 | | (negative control) 160 (positive control 1) |
| | | 6.17 | | 5.5 | | 4.5 | | 1280 (Positive control 2) |
| | | 5.83 | | 4.5 | | 5.5 | | |

The digits (eg 8-2-5) in column A denotes the D antigen units of polio Types 1-2-3 respectively. Each Guinea Pig (7A to 12 B) received three doses of combined vaccine containing IPV and 10 ug of inactivated rotavirus antigen (IRV) on day 1, Day 14 and Day 28 and the serum samples were collected on day 42. Guinea pig no 15A and 15B received three doses of live rotavirus (log 5.5FFU or 10 ug) as considered as positive control. In negative control group (17A and 17B) only the formulation containing alum without any antigen was used for immunization.

TABLE 6

SNT for Trivalent Salk + Rota 1Dose and 2 Dose

| Group 7: Salk + Rota 8-2-5 (1 Dose) | | | | Group 8: Salk + Rota 8-2-5 (2 Dose) | | | | Group 9: Salk + Rota 5-2-5 (2 Dose) | | | |
|---|---|---|---|---|---|---|---|---|---|---|---|
| Rat No | Type 1 | Type 2 | Type 3 | Rat No | Type 1 | Type 2 | Type 3 | Rat No | Type 1 | Type 2 | Type 3 |
| 1 | 2 | 7 | 7 | 1 | 10 | 8 | 11 | 1 | 3 | 9 | 12 |
| 2 | 3 | 7 | 9 | 2 | 7 | 8 | 10 | 2 | 7 | 6 | 12 |
| 3 | 4 | 7 | 8 | 3 | 7 | 7 | 7 | 3 | 7 | 8 | 10 |
| 4 | 4 | 6 | 10 | 4 | 10 | 7 | 10 | 4 | 11 | 9 | 8 |
| 5 | 0 | 7 | 8 | 5 | 9 | 7 | 12 | 5 | 5 | 6 | 10 |
| 6 | 0 | 9 | 10 | 6 | 5 | 8 | 9 | 6 | 10 | 9 | 12 |
| 7 | 5 | 7 | 10 | 7 | 5 | 6 | 10 | 7 | 6 | 6 | 12 |
| 8 | 8 | 9 | 6 | 8 | 10 | 8 | 11 | 8 | 2 | 10 | 12 |
| 9 | 4 | 8 | 5 | 9 | 6 | 9 | 11 | 9 | 9 | 9 | 10 |
| 10 | 6 | 8 | 10 | 10 | 7 | 9 | 10 | 10 | 5 | NS | NS |

TABLE 7

SNT for Trivalent Sabin + Rota 1Dose and 2 Dose

| Group 10: Sabin + Rota 5-16-10 (1 Dose) | | | | Group 11: Sabin + Rota 5-16-10 (2 Dose) | | | | Group 12: Sabin + Rota 2.5-8-5 (2 Dose) | | | |
|---|---|---|---|---|---|---|---|---|---|---|---|
| Rat No | Type 1 | Type 2 | Type 3 | Rat No | Type 1 | Type 2 | Type 3 | Rat No | Type 1 | Type 2 | Type 3 |
| 1 | 7 | 4 | 11 | 1 | 8 | 7 | 12 | 1 | 5 | 4 | 11 |
| 2 | 10 | 5 | 11 | 2 | 5 | 7 | NS | 2 | 7 | 2 | 12 |
| 3 | 7 | 3 | 10 | 3 | 8 | 4 | 12 | 3 | 6 | 6 | 9 |
| 4 | 8 | 5 | 11 | 4 | 6 | 7 | 12 | 4 | 6 | 8 | 9 |
| 5 | 7 | 4 | 11 | 5 | 8 | 7 | 12 | 5 | 7 | 5 | 8 |
| 6 | 8 | 4 | 11 | 6 | 8 | 7 | 12 | 6 | 5 | 6 | 12 |
| 7 | 6 | 3 | 12 | 7 | 8 | 4 | 10 | 7 | 8 | 6 | 10 |
| 8 | 11 | 5 | 12 | 8 | 7 | 4 | 11 | 8 | 8 | 6 | 11 |
| 9 | 7 | 7 | 10 | 9 | 8 | 4 | 12 | 9 | 10 | 7 | 12 |
| 10 | 9 | 4 | 12 | 10 | 6 | 3 | 10 | 10 | NS | NS | NS |

| Group 13: Salk Commercial (1 Dose) | | | | Group 14: Salk Commercial (2 Dose) | | | | Group No. 16 Negative Control | | | |
|---|---|---|---|---|---|---|---|---|---|---|---|
| Rat No | Type 1 | Type 2 | Type 3 | Rat No | Type 1 | Type 2 | Type 3 | Rat No | Type 1 | Type 2 | Type 3 |
| 1 | 4 | 7 | 2 | 1 | 6 | 7 | NS | 1 | 0 | 0 | 0 |
| 2 | 0 | 4 | 6 | 2 | 3 | 8 | 11 | 2 | 0 | 0 | 0 |
| 3 | 0 | 6 | 5 | 3 | 1 | 7 | 8 | 3 | 0 | 0 | 0 |
| 4 | 4 | 8 | 9 | 4 | 7 | 8 | 9 | 4 | 0 | 0 | 0 |
| 5 | 0 | 7 | 3 | 5 | 2 | 5 | 7 | 5 | 0 | 0 | 0 |

TABLE 7-continued

SNT for Trivalent Sabin + Rota 1Dose and 2 Dose

| 6  | 3 | 6 | 3 | 6  | 7  | 8 | 10 | 6  | 0 | 0 | 0 |
| 7  | 3 | 6 | 6 | 7  | 7  | 6 | 9  | 7  | 0 | 0 | 0 |
| 8  | 0 | 4 | 6 | 8  | 12 | 7 | 9  | 8  | 0 | 0 | 0 |
| 9  | 5 | 8 | 5 | 9  | 10 | 9 | 11 | 9  | 0 | 0 | 0 |
| 10 | 0 | 4 | 5 | 10 | 5  | 8 | 7  | 10 | 0 | 0 | 0 |

Result and Interpretation:
1. Bivalent vaccine (IPV+IRV) give significantly higher seroconversion on day 42 as compare to Day 0.
2. Single dose of trivalent Sabin IPV developed at SIIL having 5:16:10 DU with alum gives better seroconversion as compared to commercial IPV.
3. Double dose of trivalent Sabin IPV developed at SIIL having 2.5:8:5 DU with alum gives excellent seroconversion as compared to commercial IPV.
4. Single dose of trivalent Salk IPV formulated at SIIL having 8:2:5 DU with alum gives better seroconversion as compared to commercial IPV.
5. Double dose of trivalent Sabin IPV formulated at SIIL having 5:2:5 DU with alum gives excellent seroconversion as compared to commercial IPV.

Example 9

Hexavalent Combination Vaccine Compositions comprising Dose reduced IPV, Inactivated rotavirus, D, T, wP, and Hib PRP-Protein conjugate are as given below:

TABLE 8

Hexavalent Formulation-1 having dose reduced Salk IPV

| S. NO. | FORMULATION COMPONENTS | Formulation 1A | Formulation 1B | Formulation 1C | Formulation 1D | Formulation 1E | Formulation 1F | Formulation 1G | Formulation 1H |
|---|---|---|---|---|---|---|---|---|---|
| 1 | Diphtheria Toxoid (D) | 22.5 Lf | | | | | | | |
| 2 | Tetanus toxoid (T) | 7.5 Lf | | | | | | | |
| 3 | Inactivated *B. pertussis* antigen (wP) | 15 IOU | | | | | | | |
| 4 | Inactivated Salk Strain of Polio Virus | | | | | | | | |
|   | Type I (D antigen units) | 10 | 7.5 | 8 | 10 | 10 | 7.5 | 5 | 10 |
|   | Type II (D antigen units) | 2 | 16 | 2 | 2 | 2 | 16 | 2 | 2 |
|   | Type III (D antigen units) | 10 | 10 | 5 | 5 | 12 | 10 | 5 | 16 |
| 5 | Inactivated Rota virus (IRV) | 10 μg | | | | | | | |
| 6 | *H. Influenzae* b PRP- $CRM_{197}$ conjugate | 10 μg of PRP content | | | | | | | |
| 7 | Aluminium Content | Not more than 0.9 mg of $Al^{3+}$ | | | | | | | |
| 8 | 2-Phenoxyethanol | 3.25 mg | | | | | | | |
| 9 | L-Histidine | 1.55 mg | | | | | | | |
| 10 | WFI | q.s. | | | | | | | |

TABLE 9

Hexavalent Formulation-2 having dose reduced Salk IPV

| S. NO. | FORMULATION COMPONENTS | Formulation 2A | Formulation 2B | Formulation 2C | Formulation 2D | Formulation 2E | Formulation 2F | Formulation 2G | Formulation 2H |
|---|---|---|---|---|---|---|---|---|---|
| 1 | Diphtheria Toxoid (D) | 22.5 Lf | | | | | | | |
| 2 | Tetanus toxoid (T) | 7.5 Lf | | | | | | | |
| 3 | Inactivated *B. pertussis* antigen (wP) | 15 IOU | | | | | | | |
| 4 | Inactivated Salk Strain of Polio Virus | | | | | | | | |
|   | Type I (D antigen units) | 10 | 7.5 | 8 | 10 | 10 | 7.5 | 5 | 10 |
|   | Type II (D antigen units) | 2 | 16 | 2 | 2 | 2 | 16 | 2 | 2 |
|   | Type III (D antigen units) | 10 | 10 | 5 | 5 | 12 | 10 | 5 | 16 |
| 5 | Inactivated Rota virus (IRV) | 10 μg | | | | | | | |
| 6 | *H. Influenzae* b PRP-TT conjugate | 5 μg of PRP content | | | | | | | |
| 7 | Aluminium Content | Not more than 0.9 mg of $Al^{3+}$ | | | | | | | |
| 8 | 2-Phenoxyethanol | 3.25 mg | | | | | | | |
| 9 | L-Histidine | 1.55 mg | | | | | | | |
| 10 | WFI | q.s. | | | | | | | |

TABLE 10

Hexavalent Formulation-3 having dose reduced Sabin IPV

| S. NO. | FORMULATION COMPONENTS | Formulation 3A | Formulation 3B | Formulation 3C |
|---|---|---|---|---|
| 1 | Diphtheria Toxoid (D) | | 22.5 Lf | |
| 2 | Tetanus toxoid (T) | | 7.5 Lf | |
| 3 | Inactivated *B. pertussis* antigen (wP) | | 15 IOU | |
| 4 | Inactivated Sabin Strain of Polio Virus | | | |
| | Type I (D antigen units) | 5 | 2.5 | 5 |
| | Type II (D antigen units) | 16 | 8 | 8 |
| | Type III (D antigen units) | 10 | 5 | 10 |
| 5 | Inactivated Rota virus (IRV) | | 10 µg | |
| 6 | *H. Influenzae* b PRP-CRM$_{197}$ conjugate | | 10 µg of PRP content | |
| 7 | Aluminium Content | | Not more than 0.9 mg of Al$^{3+}$ | |
| 8 | 2-Phenoxyethanol | | 3.25 mg | |
| 9 | L-Histidine | | 1.55 mg | |
| 10 | WFI | | q.s. | |

TABLE 11

Hexavalent Formulation-4 having dose reduced Sabin IPV

| S. NO. | FORMULATION COMPONENTS | Formulation 4A | Formulation 4B | Formulation 4C |
|---|---|---|---|---|
| 1 | Diphtheria Toxoid (D) | | 22.5 Lf | |
| 2 | Tetanus toxoid (T) | | 7.5 Lf | |
| 3 | Inactivated *B. pertussis* antigen (wP) | | 15 IOU | |
| 4 | Inactivated Sabin Strain of Polio Virus | | | |
| | Type I (D antigen units) | 5 | 2.5 | 5 |
| | Type II (D antigen units) | 16 | 8 | 8 |
| | Type III (D antigen units) | 10 | 5 | 10 |
| 5 | Inactivated Rota virus (IRV) | | 10 µg | |
| 6 | *H. Influenzae* b PRP-TT conjugate | | 5 µg of PRP content | |
| 7 | Aluminium Content | | Not more than 0.9 mg of Al$^{3+}$ | |
| 8 | 2-Phenoxyethanol | | 3.25 mg | |
| 9 | L-Histidine | | 1.55 mg | |
| 10 | WFI | | q.s. | |

Example 10

Process for preparation of Hexavalent Combination Vaccine Compositions Comprising Dose reduced IPV, Inactivated rotavirus, D, T, wP, and Hib PRP-Protein conjugate is as given below:

a) IPV (Sabin/Salk strain) bulk and IRV bulk were individually adsorbed on Aluminum hydroxide, followed by pH adjustment to 6.2-6.6.
b) D was adsorbed on Aluminum phosphate, followed by pH adjustment to 5.5-6.5, addition of T and blending by agitation at room temperature for 18-24 hours.
c) The solutions obtained in step a and b were mixed, followed by pH adjustment to 6.4-6.6 and agitation at RT for 60 minutes.
d) wP antigen and Histidine were added to the above mixture, followed by agitation for 60 minutes and left in static condition for overnight at 2-8° C.
e) Hib PRP conjugate and 2-PE were added to the mixture obtained in step d at 2-8° C., followed by pH adjustment to 6.4-6.6.
f) NaCl and WFI (q.s.) were added to the mixture obtained in step e, followed by agitation for 2 hours.

Hib PRP-carrier protein conjugate prepared by using novel conjugation process and subsequently blended at low temperature in presence of a stabilizer shows greater stability with minimum free PRP release and improved immunogenicity. Also, addition of whole cell pertussis antigen at a later stage in a blend minimizes hydrolysis based degradation and provides a stable and immunogenic wP antigen.

Example 11

Heptavalent Combination Vaccine Compositions comprising Dose reduced IPV, Inactivated Rotavirus, D, T, Wp, Hbsag, and Hib PRP-Protein conjugate are as given below:

TABLE 12

Heptavalent Formulation-5 having dose reduced Salk IPV

| S. NO. | FORMULATION COMPONENTS | Formulation 5A | Formulation 5B | Formulation 5C | Formulation 5D | Formulation 5E | Formulation 5F | Formulation 5G | Formulation 5H |
|---|---|---|---|---|---|---|---|---|---|
| 1 | Diphtheria Toxoid (D) | colspan 22.5 Lf |
| 2 | Tetanus toxoid (T) | 7.5 Lf |
| 3 | Inactivated *B. pertussis* antigen (wP) | 15 IOU |
| 4 | Inactivated Salk Strain of Polio Virus | | | | | | | | |
|   | Type I (D antigen units) | 10 | 7.5 | 8 | 10 | 10 | 7.5 | 5 | 10 |
|   | Type II (D antigen units) | 2 | 16 | 2 | 2 | 2 | 16 | 2 | 2 |
|   | Type III (D antigen units) | 10 | 10 | 5 | 5 | 12 | 10 | 5 | 16 |
| 5 | Inactivated Rota virus (IRV) | 10 µg |
| 6 | *H. Influenzae* b PRP- CRM$_{197}$ conjugate | 10 µg of PRP content |
| 7 | Hepatitis B surface antigen (HbsAg) | 12.5 µg |
| 8 | Aluminium Content | Not more than 0.9 mg of Al$^{3+}$ |
| 9 | 2-Phenoxyethanol | 3.25 mg |
| 10 | L-Histidine | 1.55 mg |
| 11 | WFI | q.s. |

TABLE 7

Heptavalent Formulation-6 having dose reduced Salk IPV

| S. NO. | FORMULATION COMPONENTS | Formulation 6A | Formulation 6B | Formulation 6C | Formulation 6D | Formulation 6E | Formulation 6F | Formulation 6G | Formulation 6H |
|---|---|---|---|---|---|---|---|---|---|
| 1 | Diphtheria Toxoid (D) | 22.5 Lf |
| 2 | Tetanus toxoid (T) | 7.5 Lf |
| 3 | Inactivated *B. pertussis* antigen (wP) | 15 IOU |
| 4 | Inactivated Salk Strain of Polio Virus | | | | | | | | |
|   | Type I (D antigen units) | 10 | 7.5 | 8 | 10 | 10 | 7.5 | 5 | 10 |
|   | Type II (D antigen units) | 2 | 16 | 2 | 2 | 2 | 16 | 2 | 2 |
|   | Type III (D antigen units) | 10 | 10 | 5 | 5 | 12 | 10 | 5 | 16 |
| 5 | Inactivated Rota virus (IRV) | 10 µg |
| 6 | *H. Influenzae* b PRP-TT conjugate | 5 µg of PRP content |
| 7 | Hepatitis B surface antigen (HbsAg) | 12.5 µg |
| 8 | Aluminium Content | Not more than 0.9 mg of Al$^{3+}$ |
| 9 | 2-Phenoxyethanol | 3.25 mg |
| 10 | L-Histidine | 1.55 mg |
| 11 | WFI | q.s. |

TABLE 8

Heptavalent Formulation-7 having dose reduced Sabin IPV

| S. NO. | FORMULATION COMPONENTS | Formulation 7A | Formulation 7B | Formulation 7C |
|---|---|---|---|---|
| 1 | Diphtheria Toxoid (D) | 22.5 Lf |
| 2 | Tetanus toxoid (TT) | 7.5 Lf |
| 3 | Inactivated *B. pertussis* antigen (wP) | 15 IOU |
| 4 | Inactivated Sabin Strain of Polio Virus | | | |

TABLE 8-continued

Heptavalent Formulation-7 having dose reduced Sabin IPV

| S. NO. | FORMULATION COMPONENTS | Formulation 7A | Formulation 7B | Formulation 7C |
|---|---|---|---|---|
|  | Type I (D antigen units) | 5 | 2.5 | 5 |
|  | Type II (D antigen units) | 16 | 8 | 8 |
|  | Type III (D antigen units) | 10 | 5 | 10 |
| 5 | Inactivated Rota virus (IRV) | colspan: 10 μg | | |
| 6 | H. Influenzae b PRP-CRM$_{197}$ conjugate | colspan: 10 μg of PRP content | | |
| 7 | Hepatitis B surface antigen (HbsAg) | colspan: 12.5 μg | | |
| 8 | Aluminium Content | Not more than 0.9 mg of Al$^{3+}$ | | |
| 9 | 2-Phenoxyethanol | colspan: 3.25 mg | | |
| 10 | L-Histidine | colspan: 1.55 mg | | |
| 11 | WFI | q.s. | | |

TABLE 9

Heptavalent Formulation-8 having dose reduced Sabin IPV

| S. NO. | FORMULATION COMPONENTS | Formulation 8A | Formulation 8B | Formulation 8C |
|---|---|---|---|---|
| 1 | Diphtheria Toxoid (D) | | 22.5 Lf | |
| 2 | Tetanus toxoid (T) | | 7.5 Lf | |
| 3 | Inactivated B. pertussis antigen (wP) | | 15 IOU | |
| 4 | Inactivated Sabin Strain of Polio Virus | | | |
|  | Type I (D antigen units) | 5 | 2.5 | 5 |
|  | Type II (D antigen units) | 16 | 8 | 8 |
|  | Type III (D antigen units) | 10 | 5 | 10 |
| 5 | Inactivated Rota virus (IRV) | | 10 μg | |
| 6 | H. Influenzae b PRP-TT conjugate | | 5 μg of PRP content | |
| 7 | Hepatitis B surface antigen (HbsAg) | | 12.5 μg | |
| 8 | Aluminium Content | | Not more than 0.9 mg of Al$^{3+}$ | |
| 9 | 2-Phenoxyethanol | | 3.25 mg | |
| 10 | L-Histidine | | 1.55 mg | |
| 11 | WFI | | q.s. | |

Example 12

Process for Preparation of Heptavalent Combination Vaccine Compositions Comprising Dose Reduced IPV, Inactivated Rotavirus, D, T, Wp, Hbsag, And Hib PRP-Protein Conjugate is as Given Below a) IPV (Sabin/Salk strain) bulk and IRV bulk were individually adsorbed on Aluminum hydroxide, followed by pH adjustment to 6.2-6.6.
b) HBsAg was adsorbed on Aluminum phosphate, followed by pH adjustment to 6.0-6.5.
c) D was adsorbed on Aluminum phosphate, followed by pH adjustment to 5.5-6.5 and addition of T.
d) Mix solution obtained in step b and c, followed by blending agitation at room temperature for 18-24 hours.
e) Above mixtures [as obtained in step a and d] were added, followed by pH adjustment to 6.4-6.6 and agitation at RT for 60 minutes.
f) wP antigen and Histidine were added to the above mixture, followed by agitation for 60 minutes and left in static condition for overnight at 2-8° C.
g) Hib PRP protein conjugate and 2-PE were added to the mixture obtained in step f at 2-8° C., followed by pH adjustment to 6.4-6.6.
h) NaCl and WFI (q.s.) were added to the mixture obtained in step g, followed by agitation for 2 hours.

Hib PRP-carrier protein conjugate prepared by using novel conjugation process and subsequently blended at low temperature in presence of a stabilizer shows greater stability with minimum free PRP release and improved immunogenicity. Also, addition of whole cell pertussis antigen at a later stage in a blend minimizes hydrolysis based degradation and provides a stable and immunogenic wP antigen.

The invention claimed is:
1. A combination vaccine comprising
  i) inactivated polio virus (IPV) antigen selected from Salk or Sabin strain;
  ii) inactivated rotavirus (IRV) antigen;
  iii) optionally one or more antigens selected from group comprising of diphtheria toxoid (D), tetanus toxoid (T), whole cell pertussis (wP), HBsAg, Hib PRP-carrier protein conjugate, Neisseria meningitidis A antigen(s), Neisseria meningitidis C antigen(s), Neisseria meningitidis W-135 antigen(s), Neisseria meningitidis Y antigen(s), Neisseria meningitidis X antigen(s), Streptococcus Pneumoniae antigen(s), Neisseria meningitidis B bleb or purified antigen(s), Staphylococcus aureus antigen(s), anthrax, BCG, hepatitis A antigen(s), hepatitis B antigen, human papilloma virus, Salmonella typhi antigen(s), acellular pertussis, modified adenylate cyclase, malaria antigen (RTS,S), measles, mumps, rubella, dengue, zika, ebola, chikungunya, Japanese encephalitis, diarrheal antigens; and iv) one or more aluminum adjuvant is an aluminium salt selected from a group consisting of aluminum hydroxide and aluminum phosphate, wherein the inactivated polio virus antigen is a dose reduced inactivated polio virus antigen selected from a group consisting of i.a) a dose composition having Sabin Type 1, Type 2, Type 3 combination selected from 5-16-10 D-antigen units;

i.b) a dose composition having Sabin Type 1, Type 2, Type 3 combination selected from 2.5-8-5 D-antigen units;

i.c) a dose composition having Sabin Type 1, Type 2, Type 3 combination selected from 5-8-10 D-anti gen units;

i.d) a dose composition having Salk Type 1, Type 2, Type 3 combination selected from 7.5-16-10 D-antigen units;

i.e) a dose composition having Salk Type 1, Type 2, Type 3 combination selected from 8-2-5 D-antigen units;

i.f) a dose composition having Salk Type 1, Type 2, Type 3 combination selected from 10-2-5 D-antigen units;

i.g) a dose composition having Salk Type 1, Type 2, Type 3 combination selected from 10-2-10 D-antigen units;

i.h) a dose composition having Salk Type 1, Type 2, Type 3 combination selected from 10-2-12 D - antigen units;

i.i) a dose composition having Salk Type 1, Type 2, Type 3 combination selected from 10-2-16 D - antigen units; and i.j) a dose composition having Salk Type 1, Type 2, Type 3 combination selected from 5-2-5 D-antigen units;

wherein said dose reduced inactivated polio virus antigen is adsorbed on an aluminum hydroxide adjuvant.

2. The vaccine as claimed in claim 1, wherein said dose reduced inactivated polio virus antigen is adsorbed on the aluminum hydroxide adjuvant having $Al^{3+}$ concentration between 0.1-2.5 mg/dose and percent adsorption of at least 70%.

3. The vaccine as claimed in claim 2, wherein said dose reduced inactivated polio virus antigen is adsorbed on the aluminum hydroxide adjuvant having $Al^{3+}$ concentration between 0.1-0.7 mg/dose and percent adsorption of at least 90%.

4. The vaccine as claimed in claim 1, wherein the IRV antigen is an injectable heat inactivated rotavirus selected from CDC-9, CDC-66 or any other inactivated rotavirus strains and is adsorbed on the aluminum hydroxide adjuvant having $Al^{3+}$ concentration between 0.1-2.5 mg/dose and providing percent adsorption of at least 70%.

5. The vaccine as claimed in claim 4, wherein the IRV antigen is heat inactivated CDC-9 rotavirus strain and is adsorbed on the aluminum hydroxide adjuvant having $Al^{3+}$ concentration between 0.1-0.5 mg/dose and providing a percent adsorption of at least 90%.

6. The vaccine as claimed in claim 1, wherein the D and T antigens are adsorbed onto aluminum phosphate adjuvant.

7. The vaccine as claimed in claim 1, wherein the D and T are purified using gel permeation chromatography with resin selected from the group comprising of Sephacryl S-300 HR, PLgel, Sephacryl S-200HR, Sephadex, Bio-Gel (cross-linked polyacrylamide agarose gel) and Styragel.

8. The vaccine as claimed in claim 1, wherein the pertussis antigen is an acellular antigen comprising one or more antigens selected from modified adenylate cyclase, pertussis toxoid (PT), filamentous hemagglutinin (FHA), pertactin (P69 or PRN), and fimbrial proteins (FIM 1, 2 and 3).

9. The vaccine as claimed in claim 1, wherein the pertussis antigen is an inactivated whole cell pertussis comprising one or more of *bordetella pertussis* strains 134, 509, 25525 and 6229.

10. The vaccine as claimed in claim 1, wherein the Hib antigen is Hib PRP polysaccharide conjugated to a carrier protein using a cyanylation conjugation chemistry, wherein said cyanylation reagent is selected from 1-cyano-4-dimethylaminopyridinium tetrafluoroborate (CDAP)1-cyano-4-pyrrolidinopyridinium tetrafluorborate (CPPT), 1-cyanoimidazole namely (1-CI), 1-cyanobenzotriazole(1-CBT) or 2-cyanopyridazine-3(2H)one (2-CPO); and the carrier protein is selected from a group consisting of CRM197, diphtheria toxoid, *Neisseria meningitidis* outer membrane complex, fragment C of tetanus toxoid, pertussis toxoid, protein D of H. influenzae, *E. coli* LT, *E. coli* ST, and exotoxin A from *Pseudomonas aeruginosa*, outer membrane complex c (OMPC), porins, transferrin binding proteins, pneumolysin, pneumococcal surface protein A (PspA), pneumococcal surface adhesin A (PsaA), pneumococcal PhtD, pneumococcal surface proteins BVH-3 and BVH-11, protective antigen (PA) of *Bacillus anthracis* and detoxified edema factor (EF) and lethal factor (LF) of *Bacillus anthracis*, ovalbumin, keyhole limpet hemocyanin (KLH), human serum albumin, bovine serum albumin (BSA) and purified protein derivative of tuberculin (PPD), synthetic peptides, heat shock proteins, pertussis proteins, cytokines, lymphokines, hormones, growth factors, artificial proteins comprising multiple human CD4+T cell epitopes from various pathogen-derived antigens such as N 19, iron-uptake proteins, toxin A or B from C. difficile and *S. agalactiae* proteins.

11. The vaccine as claimed in claim 1, wherein HBsAg antigen is a surface antigen of Hepatitis B and is individually adsorbed onto aluminum phosphate.

12. The vaccine as claimed in claim 1, wherein vaccine comprises at least one preservative selected from a group consisting of benzetonium chloride, 2-phenoxyethanol, phenol, thiomersal, and formaldehyde.

13. The vaccine as claimed in claim 1, wherein the combination vaccine is a bivalent vaccine composition comprising the dose reduced IPV and inactivated IRV.

14. The vaccine as claimed in claim 13, wherein the dose concentration of Type 1, Type 2, and Type 3 of Salk strain based IPV is selected from i) 8 D antigen units, 2 D antigen units, 5 D antigen units; ii) 10 D antigen units, 2 D antigen units, 10 D antigen units; and iii) 10 D antigen units, 2 D antigen units, 16 D antigen units.

15. The vaccine as claimed in claim 13, wherein the concentration of Type 1, Type 2, and Type 3 of Sabin strain based IPV is 5-16-10 D antigen units.

16. The vaccine as claimed in claim 13, wherein concentration of IRV antigen is 10 µg/dose.

17. The vaccine as claimed in claim 13, wherein total aluminum content ($Al^{3+}$) is in the concentration not greater than 1 mg/dose.

18. The vaccine as claimed in claim 1, comprising D, T, wP, Hib, IPV antigen and IRV antigen, wherein D is present in an amount in the range of 1-50 Lf; T is present in an amount in the range of 1-30 Lf; wP is present in an amount in the range of 10-50 IOU; dose reduced inactivated Salk strain of polio virus type 1 antigen is present in an amount in the range of 1-20 D antigen units, type 2 in the range of 1-20 D antigen units, Type 3 in the range of 1-20 D antigen units; IRV is present in an amount in the range of 1-30 µg; H. influenzae type b PRP- protein conjugate is present in an amount in the range of 2-20 µg of PRP content; total aluminum content ($Al^{3+}$) is present in an amount in the range of 0.4-1.5 mg; 2-phenoxyethanol is present in an amount in the range of 2-6 mg; and L-Histidine is present in an amount in the range of 0.5-5 mg.

19. The vaccine as claimed in claim 18, comprising D, T, wP, Hib, IPV antigen and IRV antigen, wherein D is present in an amount of about 22.5 Lf; T is present in an amount of about 7.5 IOU; wP is present in an amount of about 15 IOU; dose reduced inactivated Salk strain of polio virus type 1 is present in an amount of about 10 D antigen units, type 2 is present in an amount of about 2 D antigen units, Type 3 is present in an amount of about 10 or 16 D antigen units; IRV is present in an amount of about 10 µg; H. influenzae type b PRP- TT conjugate is present in an amount of about 5 µg of PRP content; total aluminum content ($Al^{3+}$) is present in an amount of not more than 0.9 mg; 2-phenoxyethanol is present in an amount of about 3.25 mg; and L-Histidine is present in an amount of about 1.55 mg.

20. The vaccine as claimed in claim 18, comprising D, T, wP, Hib, IPV antigen and IRV antigen, wherein D is present in an amount of about 22.5 Lf; T is present in an amount of about 7.5 Lf; wP is present in an amount of about 15 IOU; dose reduced inactivated Salk strain of polio virus type 1 is present in an amount of about 10 D antigen units, type 2 is present in an amount of about 2 D antigen units, Type 3 is present in an amount of about 10 or 16 D antigen units; IRV is present in an amount of about 10 µg; H. influenzae type b PRP- CRM197 conjugate is present in an amount of about 10 µg of PRP content; total aluminum content ($Al^{3+}$) is present in an amount of not more than 0.9 mg; 2-phenoxyethanol is present in an amount of about 3.25 mg; and L-Histidine is present in an amount of about 1.55 mg.

21. The vaccine as claimed in claim 1, comprising D, T, wP, Hib, IPV antigen and IRV antigen, wherein D is present in an amount in the range of 1-50 Lf; T is present in an amount in the range of 1-30 Lf; wP is present in an amount in the range of 10-50IOU; dose reduced inactivated Sabin strain of polio virus type 1 is present in an amount in the range of 1-20 D antigen units, type 2 in the range of 1-20 D antigen units, Type 3 in the range of 1-20 D antigen units; IRV is present in an amount in the range of 1-30 µg; H. influenzae type b PRP- protein conjugate is present in an amount in the range of 2-20 µg of PRP content; total aluminum content ($Al^{3+}$) is present in an amount in the range of 0.4-1.5 mg; 2-phenoxyethanol is present in an amount in the range of 2-6 mg; and L-Histidine is present in an amount in the range of 0.5-5 mg.

22. The vaccine as claimed in claim 21, comprising D, T, wP, Hib, IPV antigen and IRV antigen, wherein D is present in an amount of about 22.5 Lf; T is present in an amount of about 7.5 Lf; wP is present in an amount of about 15 IOU; dose reduced inactivated Sabin strain of polio virus type 1 is present in an amount of about 5 D antigen units, type 2 is present in an amount of about 16 D antigen units, Type 3 is present in an amount of about 10 D antigen units; IRV is present in an amount of about 10 µg; H. influenzae type b PRP- TT conjugate is present in an amount of about 5 µg of PRP content; total aluminum content ($Al^{3+}$) is present in an amount of not more than 0.9 mg; 2-phenoxyethanol is present in an amount of about 3.25 mg; and L-Histidine is present in an amount of about 1.55 mg.

23. The vaccine as claimed in claim 21, comprising D, T, wP, Hib, IPV antigen and IRV antigen, wherein D is present in an amount of about 22.5 Lf; T is present in an amount of about 7.5 Lf; wP is present in an amount of about 15 IOU; dose reduced inactivated Sabin strain of polio virus type 1 is present in an amount of about 5 D antigen units, type 2 is present in an amount of about 16 D antigen units, Type 3 is present in an amount of about 10 D antigen units; IRV is present in an amount of about10 µg; H. influenzae type b PRP- CRM197 conjugate is present in an amount of about 10 µg of PRP content; total aluminum content ($Al^{3+}$) is present in an amount of not more than 0.9 mg; 2-phenoxyethanol is present in an amount of about 3.25 mg; and L-Histidine is present in an amount of about 1.55 mg.

24. The vaccine as claimed in claim 1, comprising D, T, wP, Hib, HBsAg, IPV antigen and IRV antigen, wherein D is present in an amount in the range of 1-50 Lf; T is present in an amount in the range of 1-30 Lf; wP is present in an amount in the range of 10-50 IOU; dose reduced inactivated Salk strain of polio virus type 1 antigen is present in an amount in the range of 1-20 D antigen units, type 2 in the range of 1-20 D antigen units, Type 3 in the range of 1-20 D antigen units; IRV is present in an amount in the range of 1-30 µg; H. influenzae type b PRP- protein conjugate is present in an amount in the range of 2-20 µg of PRP content; Hepatitis B surface antigen (HBsAg) is present in an amount in the range of 5-30 µg; total aluminum content ($Al^{3+}$) is present in an amount in the range of 0.4-1.5 mg; 2-phenoxyethanol is present in an amount in the range of 2-6 mg; and L-Histidine is present in an amount in the range of 0.5-5 mg.

25. The vaccine as claimed in claim 24, comprising D, T, wP, Hib, HBsAg, IPV antigen and IRV antigen, wherein D is present in an amount of about 22.5 Lf; T is present in an amount of about 7.5 Lf; wP is present in an amount of about 15 IOU; dose reduced inactivated Salk strain of polio virus type 1 antigen is present in an amount of about 10 D antigen units, type 2 is present in an amount of about 2 D antigen units, Type 3 is present in an amount of about 10 or 16 D antigen units; IRV is present in an amount of about10 µg; H. influenzae type b PRP- TT conjugate is present in an amount of about 5 µg of PRP content; Hepatitis B surface antigen (HBsAg) is present in an amount of about 12.5 µg; total aluminum content ($Al^{3+}$) is present in an amount of not more than 0.9 mg; 2-phenoxyethanol is present in an amount of about 3.25 mg; and L-Histidine is present in an amount of about 1.55 mg.

26. The vaccine as claimed in claim 24, comprising D, T, wP, Hib, HBsAg, IPV antigen and IRV antigen, wherein D is present in an amount of about 22.5 Lf; T is present in an amount of about 7.5 Lf; wP is present in an amount of about 15 IOU; dose reduced inactivated Salk strain of polio virus type 1 antigen is present in an amount of about 10 D antigen units, type 2 is present in an amount of about 2 D antigen units, Type 3 is present in an amount of about 10 or 16 D antigen units; IRV is present in an amount of about 10 µg; H. influenzae type b PRP- CRM197 conjugate is present in an amount of about 10 µg of PRP content; Hepatitis B surface antigen (HBsAg) is present in an amount of about 12.5 µg; total aluminum content ($Al^{3+}$) is present in an amount of not more than 0.9 mg; 2-phenoxyethanol is present in an amount of about 3.25 mg; and L-Histidine is present in an amount of about 1.55 mg.

27. The vaccine as claimed in claim 1, comprising D, T, wP, Hib, HBsAg, IPV antigen and IRV antigen, wherein D is present in an amount in the range of 1-50 Lf; T is present in an amount in the range of 1-30 Lf; wP is present in an amount in the range of 10-50 IOU; dose reduced inactivated Sabin strain of polio virus type 1 is present in an amount in the range of 1-20 D antigen units, type 2 in the range of 1-20 D antigen units, Type 3 in the range of 1-20 D antigen units; IRV is present in an amount in the range of 1-30 µg; H. influenzae type b PRP- protein conjugate is in an amount in the range of 2-20 µg of PRP content; Hepatitis B surface antigen (HBsAg) is present in an amount in the range of 5-30 µg; total aluminum content ($Al^{3+}$) is present in an amount in the range of 0.4-1.5 mg; 2-phenoxyethanol is present in an amount in the range of 2-6 mg; and L-Histidine is present in the range of 0.5-5 mg.

28. The vaccine as claimed in claim 27, comprising D, T, wP, Hib, HBsAg, IPV antigen and IRV antigen; wherein D is present in an amount of about 22.5 Lf; T is present in an amount of about 7.5 Lf; wP is present in an amount of about 15 IOU; dose reduced inactivated Sabin strain of polio virus type 1 is present in an amount of about 5 D antigen units, type 2 is present in an amount of about 16 D antigen units, Type 3 is present in an amount of about 10 D antigen units; IRV is present in an amount of about 10 µg; H. influenzae type b PRP- TT conjugate is present in an amount of about 5 µg of PRP content; Hepatitis B surface antigen (HBsAg) is present in an amount of about 12.5 µg; total aluminum content ($Al^{3+}$) is present in an amount of not more than 0.9 mg; 2-phenoxyethanol is present in an amount of about 3.25 mg; and L-Histidine is present in an amount of about 1.55 mg.

29. The vaccine as claimed in claim 27, comprising D, T, wP, Hib, HBsAg, IPV antigen and IRV antigen; wherein D is present in an amount of about 22.5 Lf; T is present in an amount of about 7.5 Lf; wP is present in an amount of about 15 IOU; dose reduced inactivated Sabin strain of polio virus type 1 is present in an amount of about 5 D antigen units, type 2 is present in an amount of about 16 D antigen units, Type 3 is present in an amount of about 10 D antigen units; IRV is present in an amount of about10 µg; H. influenzae type b PRP- CRM197 conjugate is present in an amount of about 10 µg of PRP content; Hepatitis B surface antigen (HBsAg) is present in an amount of about 12.5 µg; total aluminum content ($Al^{3+}$) is present in an amount of not more than 0.9 mg; 2-phenoxyethanol is present in an amount of about 3.25 mg; and L-Histidine is present in an amount of about 1.55 mg.

30. The vaccine as claimed in claim 1, wherein the IPV and IRV antigens are individually adsorbed on aluminum hydroxide; and other antigen(s) are either unadsorbed or adsorbed on aluminum salt selected from one or more of aluminum phosphate, aluminum hydroxide, and combinations thereof.

31. The vaccine as claimed in claim 1, wherein the vaccine optionally comprises excipients selected from the group comprising of histidine, sucrose, glycine, and sodium chloride; more preferably histidine in the concentration range of 5-40 mM.

32. A process of manufacturing a combination vaccine as claimed in claim 1, comprising the steps of:
  a) adsorbing IPV (Sabin/Salk strain) bulk and IRV bulk individually on aluminum hydroxide; and
  b) mixing monovalent bulks of IPV and IRV and keeping the mixture at 2-8° C. on rocker for 2 hours.

33. A process of manufacturing a (hexavalent) combination vaccine as claimed in claim 1, comprising the steps of:
  a) adsorbing IPV (Sabin/Salk strain) bulk and IRV bulk individually on aluminum hydroxide, followed by pH adjustment to 6.2-6.6;
  b) adsorbing D on aluminum phosphate, followed by pH adjustment to 5.5-6.5 and addition of T and blending by agitation at room temperature for 18-24 hours;
  c) adding the above mixtures, followed by pH adjustment to 6.4-6.6 and agitation at room temperature for 60 minutes;
  d) adding wP antigen and a stabilizer to the above mixture, followed by agitation for 60 minutes and left in static condition for overnight at 2-8° C.;
  e) adding Hib PRP conjugate and 2-PE to the mixture obtained in step d at 2-8° C., followed by pH adjustment to 6.4-6.6; and
  f) adding NaCl and water for injection (WFI) (q.s.) to the mixture obtained in step e, followed by agitation for 2 hours.

34. A process of manufacturing a (heptavalent) combination vaccine as claimed in claim 1, comprising the steps of:
  a) adsorbing IPV (Sabin/Salk strain) bulk and IRV bulk individually on aluminum hydroxide, followed by pH adjustment to 6.2-6.6;
  b) adsorbing HBsAg on aluminum phosphate, followed by pH adjustment to 6.0-6.5;
  c) adsorbing D on aluminum phosphate, followed by pH adjustment to 5.5-6.5 and addition of T;
  d) blending mixtures obtained in step b and c, by agitation at room temperature for 18-24 hours;
  e) adding the above mixtures, followed by pH adjustment to 6.4-6.6 and agitation at room temperature for 60 minutes;
  f) adding wP antigen and stabilizer to the above mixture, followed by agitation for 60 minutes and left in static condition for overnight at 2-8° C.;
  g) adding Hib PRP conjugate and 2-PE to the mixture obtained in step d at 2-8° C., followed by pH adjustment to 6.4-6.6; and
  h) adding NaCl and water for injection (WFI), (q.s.) to the mixture obtained in step e, followed by agitation for 2 hours.

35. The vaccine as claimed in claim 1, wherein i) said purified diphtheria toxoid and tetanus toxoid obtained by using Gel Permeation chromatography have a monomeric content of at least 80%; ii) said Hib PRP -carrier protein conjugate prepared by using cyanylation conjugation process and subsequently blended at low temperature in presence of an excipient shows greater stability with minimum free PRP release and improved immunogenicity; and iii) said whole cell pertussis antigen added at a later stage in a blend minimizes hydrolysis based degradation and provides a stable and immunogenic wP antigen.

36. The vaccine as claimed in claim 13, wherein concentration of inactivated IRV antigen is between 1-30 µg/dose.

37. The vaccine as claimed in claim 13, wherein concentration of inactivated IRV antigen is 2.5 µg/dose.

38. The vaccine as claimed in claim 13, wherein concentration of inactivated IRV antigen is 5 µg/dose.

* * * * *